US009827304B2

(12) United States Patent
Chen et al.

(10) Patent No.: US 9,827,304 B2
(45) Date of Patent: Nov. 28, 2017

(54) LIVE ATTENUATED VACCINES FOR INFLUENZA VIRUSES

(71) Applicant: The University of Hong Kong, Hong Kong (CN)

(72) Inventors: Honglin Chen, Hong Kong (CN); Min Zheng, Hong Kong (CN); Kwok-Yung Yuen, Hong Kong (CN)

(73) Assignees: THE UNIVERSITY OF HONG KONG, Hong Kong (CN); VERSITECH LIMITED, Hong Kong (CN)

( * ) Notice: Subject to any disclaimer, the term of this patent is extended or adjusted under 35 U.S.C. 154(b) by 0 days.

(21) Appl. No.: 14/940,307

(22) Filed: Nov. 13, 2015

(65) Prior Publication Data

US 2016/0136261 A1 May 19, 2016

Related U.S. Application Data

(60) Provisional application No. 62/079,227, filed on Nov. 13, 2014.

(51) Int. Cl.

| | |
|---|---|
| ***A61K 39/145*** | (2006.01) |
| ***C12N 7/04*** | (2006.01) |
| ***C12N 7/00*** | (2006.01) |
| ***A61K 39/12*** | (2006.01) |
| *A61K 39/00* | (2006.01) |

(52) U.S. Cl.

CPC ............ *A61K 39/145* (2013.01); *A61K 39/12* (2013.01); *C12N 7/00* (2013.01); *C12N 7/04* (2013.01); *A61K 2039/5254* (2013.01); *C12N 2760/16121* (2013.01); *C12N 2760/16134* (2013.01); *C12N 2760/16162* (2013.01); *C12N 2760/16171* (2013.01)

(58) Field of Classification Search

None

See application file for complete search history.

(56) References Cited

PUBLICATIONS van Wielink et al. Mutations in the M-gene segment can substantially increase replication efficiency of NS1 deletion influenza a virus in MDCK cells. J Virol. 2012. 86:12341-12350.*

* cited by examiner

*Primary Examiner* — Nianxiang Zou

(74) *Attorney, Agent, or Firm* — Saliwanchik, Lloyd & Eisenchenk

(57) ABSTRACT

The subject invention pertains to attenuated influenza viruses, and related vaccines and methods, comprising a genetically modified viral genome. The genetically modified viral genome comprises a disruption in the non-structural (NS1) coding segment and one or more base substitution in the matrix membrane protein coding segment. The genetic modifications result in viruses that lose NS1 functionality, yet remain replication competent.

18 Claims, 17 Drawing Sheets

LIVE ATTENUATED VACCINES FOR INFLUENZA VIRUSES

CROSS-REFERENCE TO RELATED APPLICATION

This application claims the benefit of U.S. provisional application Ser. No. 62/079,227, filed Nov. 13, 2014, which is herein incorporated by reference in its entirety.

BACKGROUND OF THE INVENTION

Annual epidemics and pandemics of influenza (flu) cause significant disease burden and excess mortality due to complications globally. Vaccination with flu vaccine is considered to be the most effective way to alleviate disease burden and mortality caused by influenza, as well as to prevent future pandemics in humans. Currently there are two types of flu vaccines in the market, split vaccines and cold-adapted attenuated vaccines. Pitfalls from both vaccines have long been recognized. Current split flu vaccines have low immunogenicity and cannot be ready in a short timeframe in response to the rapidly emerging strains, such as the H1N1 strain, which caused the 2009 pandemic. Poor immunogenicity has been well known for the split vaccine, in particular among old adults and young children. On the other hand, cold attenuated vaccines are only allowed for use in people between 2 to 49 years old. These problems have limited the benefits of flu vaccines for the population that needs them most. The quick production of low cost, abundant, and effective vaccines (capable of inducing a more robust immune response) is ideal for intervention and prevention of influenza, particularly seasonal influenza in young children and the elderly.

Since the emergence of human infections with avian H5N1 virus in Hong Kong in 1997, human infections with other subtypes of avian influenza virus, including H9N2, H7N7, H6N1 H7N9, H5N6, and H10N8, have been reported in countries in which these subtypes of avian influenza virus are circulating in poultry. Among these emerging influenza viruses, 650 human infections with H5N1 virus have since been identified from 16 countries, among these 386 were fatal (see, world wide website: who.int/influenza/human_animal_interface/EN_GIP_20140124 CumulativeNumberH5N1cases.pdf?ua=1). Most recently, the emergence of H7N9 virus in China in 2013 has caused 450 human cases, 165 of which were fatal (http://www.who.int/influenza/human_animal_interface/influenza_h7n9/riskassessment_h7n9_27june14.pdf).

Human infections with other novel subtypes of avian influenza virus, such as H10N8 and H5N6, were also reported in China. There is a concern that some of these subtypes may gain further adaptation in humans or become reassortant with seasonal flu virus and cause a new pandemic. The experience of the 2009 pandemic of H1N1 showed preparation of vaccine for human vaccination from the emergence of a virus takes more than 6 months before availability to the public. Current flu vaccine development will not meet the requirement for the nature of rapid dissemination of pandemic influenza. It is a certainty that there will be new pandemics in the future; however, it is impossible to predict the timing and subtype of virus.

Novel live attenuated influenza (flu) vaccines would meet the requirements for seasonal and pandemic vaccines. Live attenuated flu vaccines have several advantages over the split or inactivated vaccines. Firstly, live attenuated vaccines are able to induce better immune response in recipients; secondly, live attenuated vaccines use less vaccine for immunization; finally, attenuated live flu vaccines can be easily applied through nasal administration.

BRIEF SUMMARY OF THE INVENTION

The development of a new vaccine technology to meet the requirements of pandemic preparedness is extremely important. As such, the present invention provides attenuated influenza viruses and vaccine formulations that can be quickly and easily produced.

In one aspect, the present invention provides an attenuated influenza virus comprising a genetically modified viral genome. The genetically modified viral genome comprises a disruption in the non-structural (NS1) coding segment and one or more base substitutions in the matrix membrane protein coding segment.

In another aspect, the present invention provides a vaccine formulation comprising an attenuated influenza virus and a pharmaceutically acceptable carrier, the virus comprising a disruption in the NS1 coding segment of the viral genome and one or more base substitutions in the matrix membrane protein coding segment of the viral genome.

In another aspect, the present invention provides methods for generating an attenuated influenza virus comprising: introducing a disrupted coding sequence of an influenza virus NS1 gene into a cell or egg; introducing a matrix membrane coding sequence of an influenza virus into the cell or egg, wherein the matrix membrane coding sequence comprises one or more base substitutions and wherein the cell or egg comprises the remaining influenza virus gene segments and viral proteins required to produce influenza virus particles; and culturing the cell or egg, wherein the attenuated influenza virus is replicated.

In yet another aspect, the present invention provides methods for inducing an immune response against an influenza virus, comprising administering to a subject an effective amount of a vaccine formulation comprising a genetically engineered attenuated influenza virus and a pharmaceutically acceptable carrier, in which the genome of the genetically engineered attenuated influenza virus encodes a disrupted NS1 protein and one or more matrix membrane proteins with one or more missense mutations.

In some embodiments of the aspects provided, the disruption in the NS1 coding segment is a deletion resulting in a knockout of the encoded NS1 protein. The attenuated influenza virus can be generated from influenza virus strains, such as but not limited to, H7N9, H1N1, and H5N1. In some embodiments of the viruses, formulations and methods provided, the base substitutions are selected from a G917A substitution, an A14U substitution, and combinations thereof.

The methods and compositions herein described can be used in connection with pharmaceutical, medical, and veterinary applications, as well as fundamental scientific research and methodologies, as would be apparent to a skilled person upon reading of the present disclosure. These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying figures.

BRIEF DESCRIPTION OF THE SEQUENCES

Figure 1:
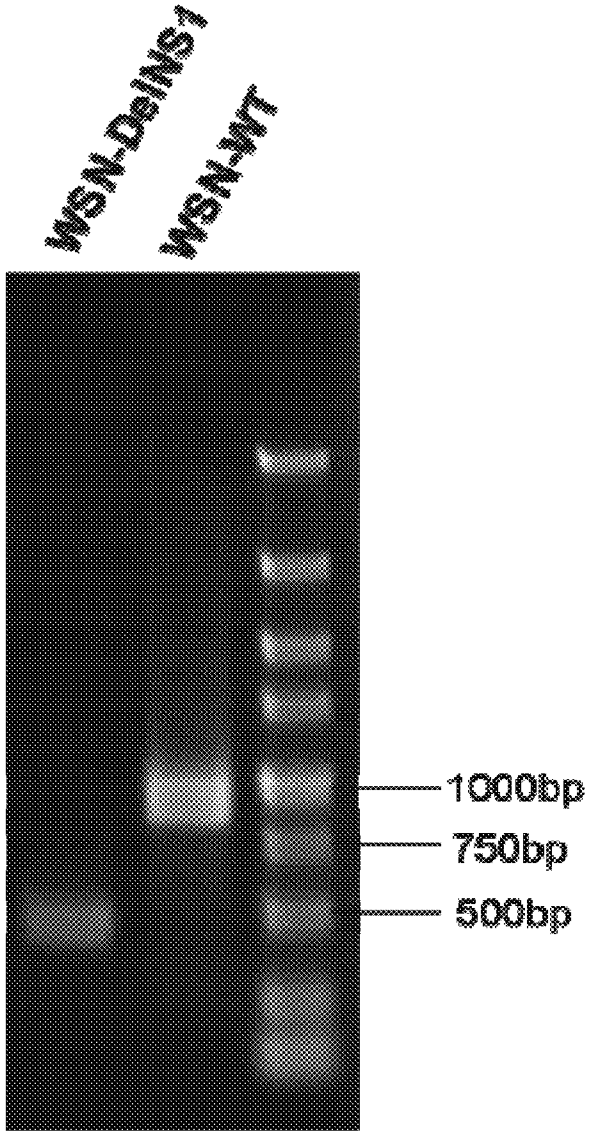
FIG. 1 shows results of a DNA agarose gel confirming deletion of the NS1 gene in the NS1-del recombinant virus (WSN-DelNS1) versus wild-type (WSN-WT).

SEQ ID NO: 1: NS-529F, the forward primer for the inverse PCR to delete the exon of the NS gene. (5'-GACATACTGATGAGGATGTCAAAAATG-3')

SEQ ID NO: 2: NS-56R, the reverse primer for the inverse PCR to delete the exon of the NS gene. (5'-CTGAAAGCTTGACACAGTGTTTGG-3')

SEQ ID NO: 3: M-478F, the forward primer for real time PCR for WSN-M1 and PR8-M1. (5'-CGGTCTCATAGGCAAATGGT-3')

SEQ ID NO: 4: M-616R, the reverse primer for real time PCR for WSN-M1. (5'-CAATATCCATGGCCTCTGCT-3')

SEQ ID NO: 5: WSN-M2-F, the forward primer for real time PCR for WSN-M2 and PR8-M2. (5'-CCGAGGTC-GAAACGCCTATC-3')

SEQ ID NO: 6: WSNM2-R, the reverse primer for real time PCR for WSN-M2, WSN-mRNA3 and WSN-M4. (5'-CTCTGGCACTCCTTCGGTAG-3')

SEQ ID NO: 7: WSN-mRNA3-F, the forward primer for real time PCR for WSN-MRNA3 and PR8-mRNA3. (5'-AGCAAAAGCAGGCCTATC-3')

SEQ ID NO: 8: WSN-M4, the forward primer for real time PCR for WSN-M4. (5'-ACCGATCTTGAGGC-CTATC-3')

SEQ ID NO: 9: The reverse primer for real time PCR for PR8-M1. (5'-CAACCTCCATGGCCTCTGCT-3')

SEQ ID NO: 10: The reverse primer for PR8-M2 and PR8-mRNA3. (5'-CTTTGGCACTCCTTCCGTAG-3')

SEQ ID NO: 11: NP-625F, the forward primer for real time PCR for WSN-NP. (5'-GGTGAGAATGGACGGA-GAAC-3')

SEQ ID NO: 12: NP-738R, the forward primer for real time PCR for WSN-NP. (5'-CCGGCTCTCTCTCACTT-GAT-3')

SEQ ID NO: 13: The forward primer for real time PCR of canine IFN-β (5'-CCAGTTCCAGAAGGAGGACA-3')

SEQ ID NO: 14: The reverse primer for real time PCR of canine IFN-β. (5'-CCTGTTGTCCCAGGTGAAGT-3')

SEQ ID NO: 15: The forward primer for real time PCR of canine β-actin (5'-CCCAAGGCCAACCGCGAGAAGAT-3')

SEQ ID NO: 16: The reverse primer for real time PCR of canine β-actin. (5'-GTCCCGGCCAGCCAGGTCCAG-3')

SEQ ID NO:17: nucleotide sequence of H1N1 M segment with A14U substitution.

SEQ ID NO:18: nucleotide sequence of H7N9 M segment with G917A substitution.

DETAILED DISCLOSURE OF THE INVENTION

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

The present invention provides methods of preparing live attenuated influenza A vaccine strains with knockout of the key virulent gene, the influenza A virus interferon antagonist, non-structural protein (NS1), designated herein as NS1-del and DelNS1; the terms may be used interchangeably. Knockout of the NS1 protein provides two advantages. Firstly, the virus strain is avirulent to humans; secondly, it is more important that the NS1-del vaccine can induce a much better immune response from the host since NS1 is a strong antagonist to both innate adaptive immunities. Typically, the influenza A virus with knockout of the NS1 gene is unable to grow well in cells or eggs, such as embryonated chicken eggs; however, the present invention provides mechanisms for compensating for this defect in virus replication through mutations, such as at A14U or G917A, in the segment of the virus genome that codes for matrix membrane proteins. As a result, the present invention provides a novel way to generate an attenuated vaccine which is avirulent to humans and can be produced in a short time for application in prevention of seasonal and pandemic influenza.

In one aspect, the present invention provides an attenuated influenza virus comprising a genetically modified viral genome. The genetically modified viral genome comprises a disruption in the non-structural (NS1) coding segment and one or more base substitutions in the matrix membrane protein coding segment. The genetic modifications result in a virus that has no NS1 protein; yet, the virus retains its viral replication abilities (due to the base substitution(s) in the matrix membrane protein coding segment compensating for NS1 loss).

In another aspect, the present invention provides a vaccine formulation comprising an attenuated influenza virus and a pharmaceutically acceptable carrier, the virus comprising a disruption in the NS1 coding segment of the viral genome and one or more base substitution in the matrix membrane protein coding segment of the viral genome.

As used herein, the term "vaccine" or "vaccine formulation" refers to a composition that stimulates an immune response to a particular antigen or antigens (i.e., influenza virus). Thus, a vaccine refers to a composition that is administered to a subject with the goal of establishing an immune response and/or immune memory to a particular influenza virus. It is also contemplated that the vaccine compositions can comprise other substances designed to increase the ability of the vaccine to generate an immune response. It is also contemplated that the present invention can provide more than one attenuated virus in the mixtures of compositions herein disclosed. For example, a mixture can comprise an attenuated H1N1 virus and an attenuated H5N1 virus. Also, the disclosed methods can comprise the simultaneous or separate administration of multiple vaccines. Thus, the present invention further includes the administration of a second, third, fourth, etc. attenuated virus; wherein the second, third, fourth, etc. attenuated virus is administered in a separate vaccine for administration at the same time as or 1, 2, 3, 4, 5, 6, 10, 14, 18, 21, 30, 60, 90, 120, 180, 360 days (or any number of days in between) after the first attenuated virus.

The term "pharmaceutically acceptable," as used herein with regard to compositions and formulations, means approved by a regulatory agency of the Federal or a state government or listed in the U.S. Pharmacopeia or other generally recognized pharmacopeia for use in animals and/or in humans.

The term "carrier" refers to a diluent, excipient, and/or vehicle with which the compositions described herein are administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include, but are not limited to, starch, glucose, sucrose, gelatin, lactose, malt, rice, flour, chalk, silica gel, sodium stearate, glycerol monostearate, talc, sodium chloride, glycerol, propylene, glycol, water, ethanol and the like. The compositions and formulations described herein may also contain wetting or emulsifying agents or suspending/diluting agents, or pH buffering agents, or agents for modifying or maintaining the rate of release of the composition. Formulations can include standard carriers such as pharmaceutical grades of mannitol, lactose, sodium saccharine, starch, magnesium stearate, cellulose, magnesium carbonate, etc. Such compositions and vaccines will contain an effective amount of the attenuated virus together with a suitable amount of carrier so as to provide the proper form to the patient based on the mode of administration to be used.

If for intravenous administration, the vaccines and compositions can be packaged in solutions of sterile isotonic aqueous buffer. Where necessary, the composition may also include a solubilizing agent. The components of the composition are supplied either separately or mixed together in unit dosage form. If the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to injection. The vaccines and compositions may also be administered to the subject intranasally, intratracheally, orally, intradermally, intramuscularly, intraperitoneally, or subcutaneously.

In another aspect, the present invention provides methods for generating an attenuated influenza virus comprising: introducing a disrupted coding sequence of an influenza virus NS1 gene into a cell or egg; introducing a matrix membrane coding sequence of an influenza virus into the cell or egg, wherein the matrix membrane coding sequence comprises one or more base substitutions and wherein the cell or egg comprises the remaining influenza virus gene segments and viral proteins required to produce influenza virus particles; and culturing the cell or egg, wherein the attenuated influenza virus is replicated. The NS1 disruption, in combination with the one or more base substitutions in the matrix membrane coding sequence, results in attenuated influenza viruses that retain their abilities to replicate in the host cell or egg.

In yet another aspect, the present invention provides methods for inducing an immune response against an influenza virus, comprising administering to a subject an effective amount of a vaccine formulation comprising a genetically engineered attenuated influenza virus and a pharmaceutically acceptable carrier, in which the genome of the genetically engineered attenuated influenza virus encodes a disrupted NS1 protein and one or more matrix membrane proteins with one or more missense mutations.

As used herein, the term "subject" refers to an animal. Typically, the terms "subject" and "patient" may be used interchangeably herein in reference to a subject. As such, a "subject" includes an animal that is being immunized, or the recipient of a mixture of components as described herein, such as an attenuated viral vaccine. The term "animal," includes, but is not limited to, mouse, rat, dog, guinea pig, cow, horse, chicken, cat, rabbit, pig, monkey, chimpanzee, and human.

The term "effective amount," as used herein, refers to an amount that is capable of inducing the necessary immune response or otherwise capable of producing an intended therapeutic effect.

In some embodiments of the viruses, vaccine formulations, and methods of the present invention, the disruption in the NS1 coding segment is a deletion resulting in a knockout of the encoded NS1 protein. In other embodiments, the disruption in the NS1 coding segment results in a truncated protein. The truncated NS1 protein loses, at least, the ability to inhibit expression of interferon β in infected cells.

In some embodiments, the attenuated influenza virus can be generated from influenza A virus strain such as, but not limited to, H7N9, H1N1, and H5N1.

In some embodiments, the base substitutions in the matrix membrane coding sequence of the influenza virus are selected from a G917A substitution, an A14U substitution, and combinations thereof. Such base substitutions result in encoded matrix membrane protein products containing one or more missense mutations. These mutations result in mutant matrix membrane protein products that compensate for the loss of NS1 function, resulting in at least partial rescue of viral replication in cells and/or eggs. In some embodiments, the rescue level of viral replication in the attenuated viruses is comparable to wild-type live viruses.

Materials and Methods

Cells and Viruses

Human embryonic kidney (HEK) 293T (ATCC) and Vero cells (ATCC) were cultured at 37° C. in Dulbecco's minimal essential medium (DMEM) supplemented with 10% fetal bovine serum, 100 units/ml penicillin, and 100 μg/ml streptomycin sulfate (Life Technologies), while MDCK (ATCC) cells were grown in Eagle's minimal essential medium (MEM) supplemented with the same amounts of serum and antibiotics. Influenza A viruses were rescued by reverse genetics and amplified in MDCK cells, as described previously. Viruses were purified using Amicon Ultra-15 centrifugal filter units (100 KD) (Millipore) to remove the cytokines in the medium. Sendai virus (SeV) was propagated in embryonated chicken eggs.

Plasmid Construction

Inverse PCR was carried out to delete the exon of the NS gene inserted into the pHW2000 vector and the plasmid was phosphorylated and self-ligated. Primers for inverse PCR were 5'-GACATACTGATGAGGATGTCAAAAATG-3' (NS-529F, SEQ ID NO: 1) and 5'-CTGAAAGCTTGACACAGTGTTTGG-3' (NS-56R, SEQ ID NO: 2). For point mutations, the QuikChange II site-directed mutagenesis kit (Stratagene) was used.

Passage of the DelNS1 Virus

Blind serial passage of the DelNS1 virus was performed in this study. The DelNS1 virus was first rescued by cotransfecting eight pHW2000 plasmids containing the eight segments of the influenza virus genome into a HEK293T/MDCK mixed cell culture; the supernatant was subsequently collected at 72 h post-transfection and designated passage 0 (P0) virus. The P0 virus obtained from the rescue procedure was used to infect MDCK cells in a T25 flask at 37° C. Two or three days later, the supernatant was transferred to infect fresh MDCK cells. Virus titers were measured at each passage. After 5 passages, when the virus titer in the subculture had stabilized, a full genome sequence of each of the DelNS1 virus passages was obtained and analyzed.

Reporter Assay

HEK293T cells were seeded onto 48-well plates and cotransfected with 50 ng each of the tested plasmids and firefly luciferase reporter containing noncoding regions from the M segment, together with 10 ng Renilla luciferase reporter as a control. After 24 h of culture, luciferase activity was measured according to the manufacturer's instructions (Promega). For the IFN-β promoter activity reporter assay, cells were infected with the indicated viruses at a multiplicity of infection (MOI) of 1 (influenza A virus) or 50 HA units (SeV) at 24 h post-transfection. Firefly luciferase values were normalized using the Renilla luciferase values.

Growth Kinetics

MDCK or Vero cells at 80 to 100% confluence seeded in 24-well plates were infected with the indicated viruses at an MOI of 0.1. After absorption for 1 h, the supernatant was removed and cells washed twice with 500 μl phosphate-buffered saline (PBS). Infected cells were overlaid with MEM containing 1 μg/ml tosylsulfonyl phenylalanyl chloromethyl ketone (TPCK)-treated trypsin (Sigma) and incubated at 37° C. Supernatants were collected at the indicated time points and the virus titer determined by plaque assay in MDCK cells.

Plaque Assay

Tenfold serial dilutions of each virus to be tested were made in MEM. Confluent MDCK cells seeded onto 6-well plates were inoculated with virus for adsorption at 37° C. for 1 h before supernatant was removed. Cells were washed twice with PBS and then overlaid with 1% MEM agarose containing 1 μg/ml TPCK-treated trypsin. Plates were placed upside down in a 37° C. incubator for 48 h. Plates were then fixed with 25% formalin for at least 2 h at room temperature. After staining with 1% crystal violet in 20% ethanol, plates were washed with tap water to remove excess dye. Plaques were visualized with the naked eye and counted. The plaque assay detected influenza virus at concentrations of >1 PFU/ml.

Western Blotting

MDCK cells were infected with the indicated viruses at an MOI of 5 and lysed at different time points with cell lysis buffer (50 mM Tris-HCl, 150 mM NaCl, and 1% Triton X-100, pH 7.4). Cell debris was discarded after centrifugation at a speed of 12,000 g for 15 min. Native polyacrylamide gel electrophoresis (NPAGE) was performed as follows. 7 to 8% polyacrylamide gel was made without the addition of SDS and with the stacking gel omitted.

Samples for N-PAGE were lysed with the passive lysis buffer used in the luciferase assay. After mixing with 5× loading buffer (1MTris-HCl [pH 6.8], 50% glycerol, 1% bromophenol blue), samples were either stored at −80° C. or analyzed immediately, with the gel being pre-run for 30 min at a constant current of 40 mA at 4° C. before loading samples. Gels were then processed in a manner similar to that for SDS-PAGE. Mouse monoclonal anti-M1 (sc-57881) and rabbit polyclonal anti-IRF3 (sc-9082) antibodies were purchased from Santa Cruz Biotechnology. Mouse monoclonal anti-M2 (ab5416) was purchased from Abcam. Mouse monoclonal anti-β-tubulin was purchased from Sigma. NP, HA, and NS1 were detected using laboratory-made antibodies at dilutions of 1:5,000, 1:3,000, and 1:5, 000, respectively.

Quantitative Real-Time PCR (qRT-PCR)

At the indicated time points after infection or transfection, total RNA was isolated using RNAiso (TaKaRa). DNA contamination was removed by DNase (Ambion) treatment. Approximately 200 ng total RNA was reverse transcribed using a high-capacity cDNA reverse transcription kit (Life Technologies). The Uni12 and oligo(dT) primers were used for preparing mRNA and vRNA, respectively, in reverse transcription reactions. The SYBR Premix Ex Taq kit (TaKaRa) was used for real-time PCR. Primers for WSN-M1 were 5'-CGGTCTCATAGGCAAATGGT-3' (M-478F, SEQ ID NO: 3) and 5'-CAATATCCATGGCCTCTGCT-3' (M-616R, SEQ ID NO: 4). Primers for WSN-M2 were 5'-CCGAGGTCGAAACGCCTATC-3' (WSN-M2-F, SEQ ID NO: 5) and 5'-CTCTGGCACTCCTTCGGTAG-3' (WSNM2-R, SEQ ID NO: 6). The forward primer for WSN-mRNA3 was 5'-AGCAAAAGCAGGCCTATC-3' (WSN-mRNA3-F, SEQ ID NO: 7), and the forward primer for WSN-M4 was 5'-ACCGATCTTGAGGCCTATC-3' (SEQ ID NO: 8). The reverse primer used for WSN-mRNA3 and WSN-M4 was WSN-M2-R. The forward primer for PR8-M1 was the same as the WSN-M1 forward primer, M-478F, and the reverse primer was 5'-CAACCTCCATGGCCTCTGCT-3' (SEQ ID NO: 9). The reverse primer for PR8-M2 and PR8-mRNA3 was 5'-CTTTGGCACTCCTTCCGTAG-3' (SEQ ID NO: 10), and forward primers were WSN-M2-F and WSN-mRNA3-F, respectively. Primers for WSN-NP were 5'-GGTGAGAATGGACGGAGAAC-3' (NP-625F, SEQ ID NO: 11) and 5'-CCGGCTCTCTCTCACTTGAT-3' (NP-738R, SEQ ID NO: 12). Primers for canine IFN-β were 5'-CCAGTTCCAGAAGGAGGACA-3' (forward, SEQ ID NO: 13) and 5'-CCTGTTGTCCCAGGTGAAGT-3' (reverse, SEQ ID NO: 14).

Primers for canine β-actin were 5'-CCCAAGGCCAACCGCGAGAAGAT-3=(forward, SEQ ID NO: 15) and 5'-GTCCCGGCCAGCCAGGTCCAG-3' (reverse, SEQ ID NO: 16).

The relative mRNA levels were analyzed using an established protocol. The amplification specificity of qRT-PCR was confirmed by melting curve analysis at the end of each program.

Mouse Infection

Mouse experiments were performed using 6 to 8 week old female BALB/c mice. To determine viral replication in lung tissues, groups of 3 mice were infected intranasally with $1\times10^4$ PFU of WSN-WT, WSN-DelNS1-M-WT, or WSN-DelNS1-M-A14U virus, diluted in 25 μl of PBS. Three days later, mice were euthanized and the lungs removed for homogenization in 1 ml PBS. Viral titers were then determined by plaque assay in MDCK cells. To determine the pathogenicity of the viruses, groups of 6 mice were inoculated intranasally with $5\times10^4$ PFU of wild-type (WT) or DelNS1-M-A14U virus in 25 μl of PBS or with PBS alone, and the body weights of infected and control group mice were recorded daily for 14 days. Mice with body weight losses of greater than 25% of the initial body weight were euthanized, in accordance with animal ethics guidelines.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Substitutions in the M Segment for Virus Replication in NS1-Del Virus To obtain NS1-del virus strains, full length NS genome segment NS derived respectively from H1N1, H7N9 and H5N1 were cloned in the pHW2000 vector. The coding region of the NS1 was knocked out by a mutagenesis protocol, while intact NS2 (or NEP) was retained in the genome segment. (FIG. 1) The NS1-del virus was rescued via co-transfection of 8 segments of each virus into 293T cells. The resulting rescued virus (very low in titer or even un-detectable by conventional assay) was blindly passaged in A549 or VERO cells. Supernatants were collected for titration and sequencing analysis. Once the virus titer was stabilized in the passage, sequences from each passage were compared. Sequences from all 8 segments were compared with the parental genome and substitutions were identified.

Figure 2:
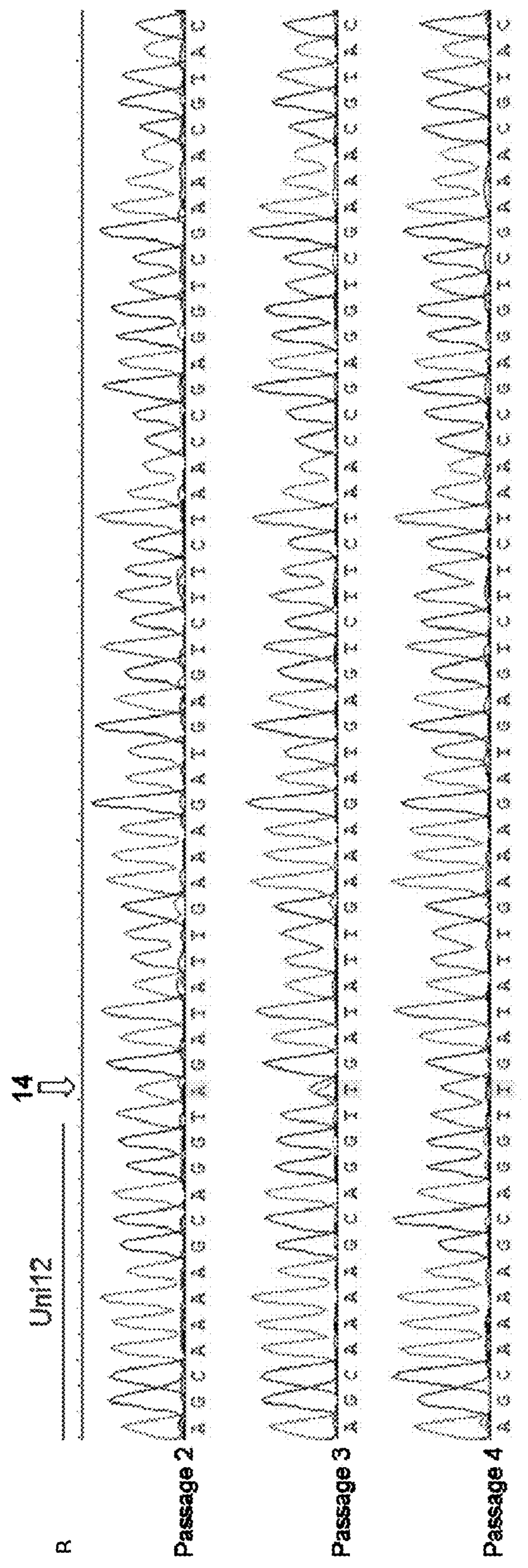
FIG. 2 shows sequencing data indicating the substitution in the M segment of the H1N1 (A/Wisconsin/1/33) strain with deleted NS1 after several passages in cells. H1N1 NS1-del virus was passaged in cells and virus genome was sequenced after passaged viruses were stabilized. A single substitution, A14U, was identified in the M segment of NS1-del H1N1 virus.
Figure 3:
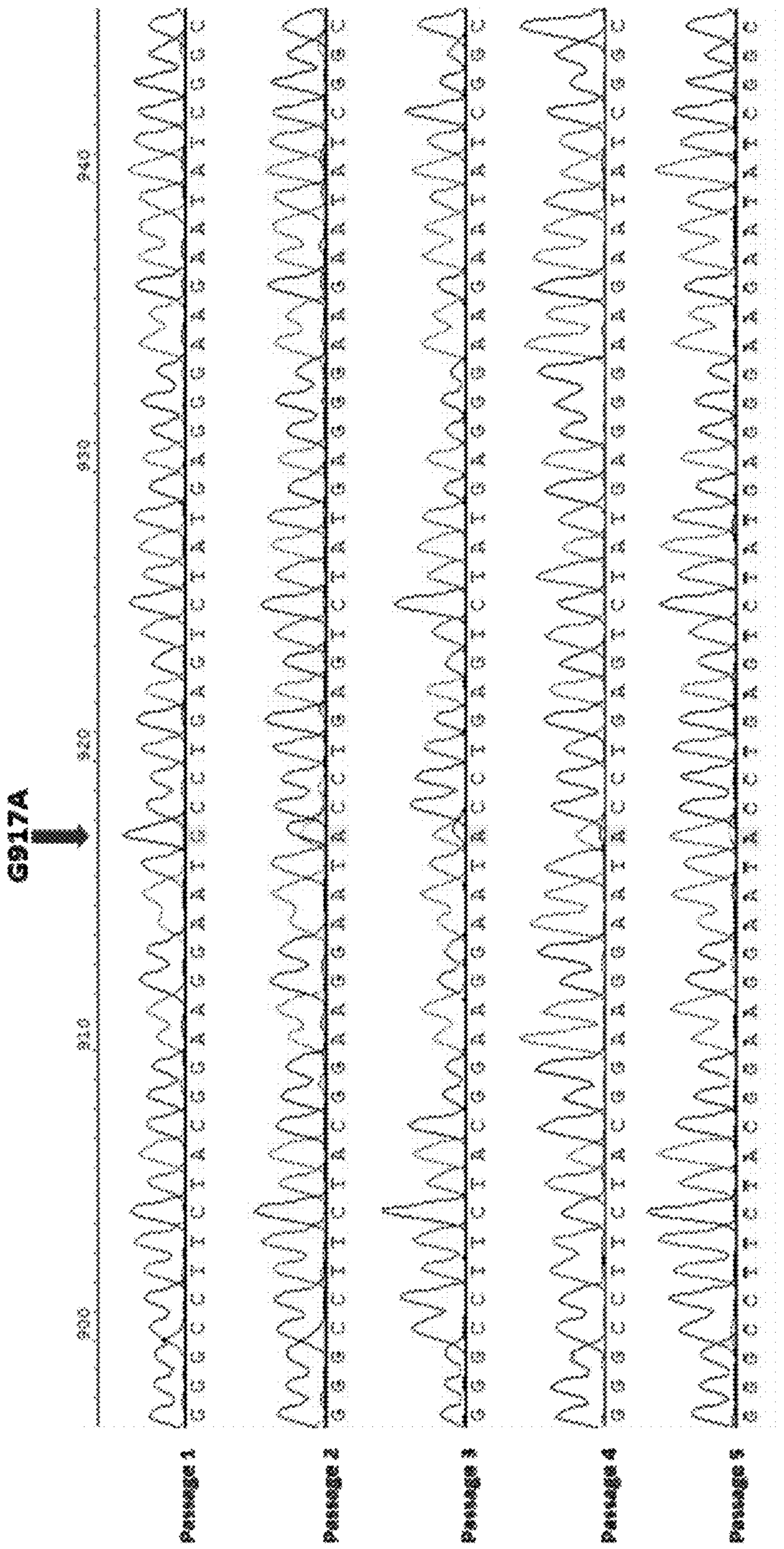
FIG. 3 shows sequencing data indicating the substitution, in the M segment of H7N9 virus, with deleted NS1 after several passages in cells. H7N9 NS1-del virus was passaged in cells and virus genome was sequenced after passaged viruses were stabilized. A single substitution, G917A, was identified in the M segment of NS1-del H7N9 virus.

Two substitutions in the M segment, namely A14U in the H1N1 and G917A in the H7N9, were consistently observed in the repeated experiments (FIGS. 2 and 3).

Figure 4:
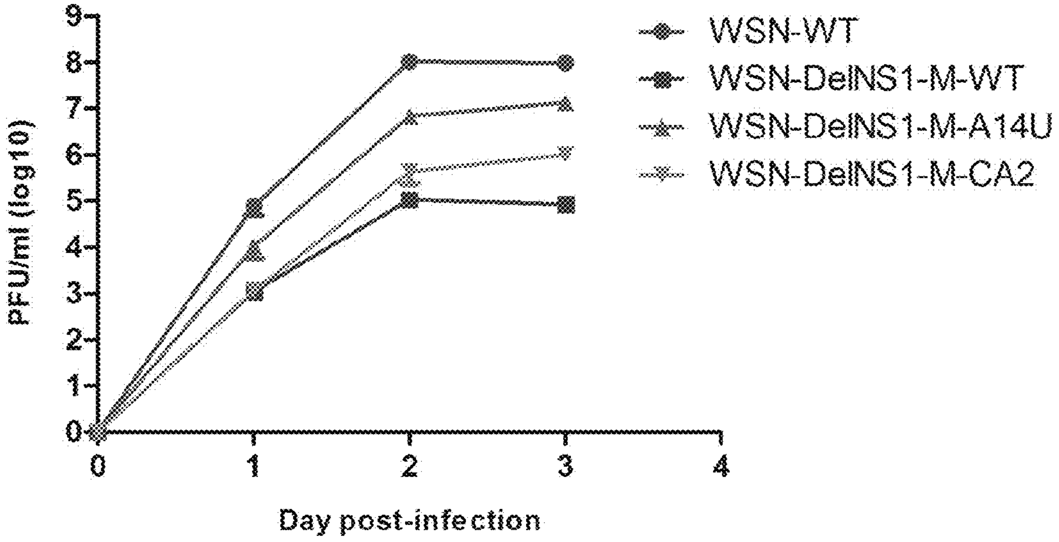
FIG. 4 is a graph showing the growth properties of H1N1 NS1-del and wild type H1N1 viruses in Vero cells. Growth ability of H1N1 NS1-del viruses were estimated and compared with wild type virus (WSN-WT). WSN-delNS1-M-WT, WSN-delNS1-A14U and WSN-delNS1-M-CA2 are NS1 deleted viruses which contain the M segment with WT, A14U and CA2 substitutions, respectively. CA2 is used as a reference strain as it has been described in PR8 virus previously (Wielink et al., 2012, *J. Virol* 86(22): 12341.). In this experiment, Vero cells were infected with WSN WT or various NS1-deleted variants (at 0.001 MOI) respectively. Virus titers (pfu) were estimated at different time points (day post infection) by plaque assay using MDCK cells. As shown in the figure, we found WSN-delNS1-A14U virus replicated much higher titer than delNS1-M-WT and WSN-delNS1-M-CA2 in Vero cells.
Figure 5:
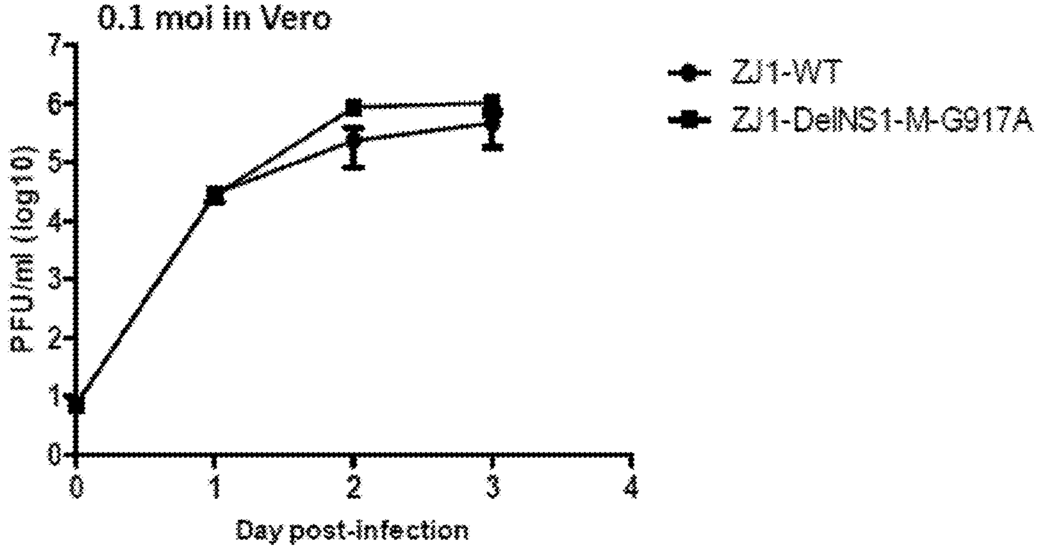
FIG. 5 is a graph showing the growth properties of NS1-del and wild type H7N9 viruses in Vero cells. Growth ability of H7N9 NS1-del virus (ZJ1-DelNS1-M-G917A) was estimated and compared with wild type virus (ZJ1-WT).

Example 2—Characterization of Growth of NS1-Del Virus with Substitution in the M Segment Growth kinetics of NS1-del viruses, versus wild type counterparts, derived from H1N1 (WSN strain) (FIG. 4) and H7N9 (Zhejiang Strain) (FIG. 5) were analyzed in various cell lines, including MDCK, VERO and A549. It was found that NS1-del viruses are able to grow to certain levels in MDCK or VERO cells. WSN-delNS1-A14U virus replicated to a much higher titer than delNS1-M-WT and WSN-delNS1-M-CA2 in Vero cells. NS1-del viruses were further evaluated using chicken embryonated eggs, and it was shown that these viruses are able to propagate in eggs.

Example 3—Characterization of Antagonism of Interferon of NS1-Del Virus

Figure 6:
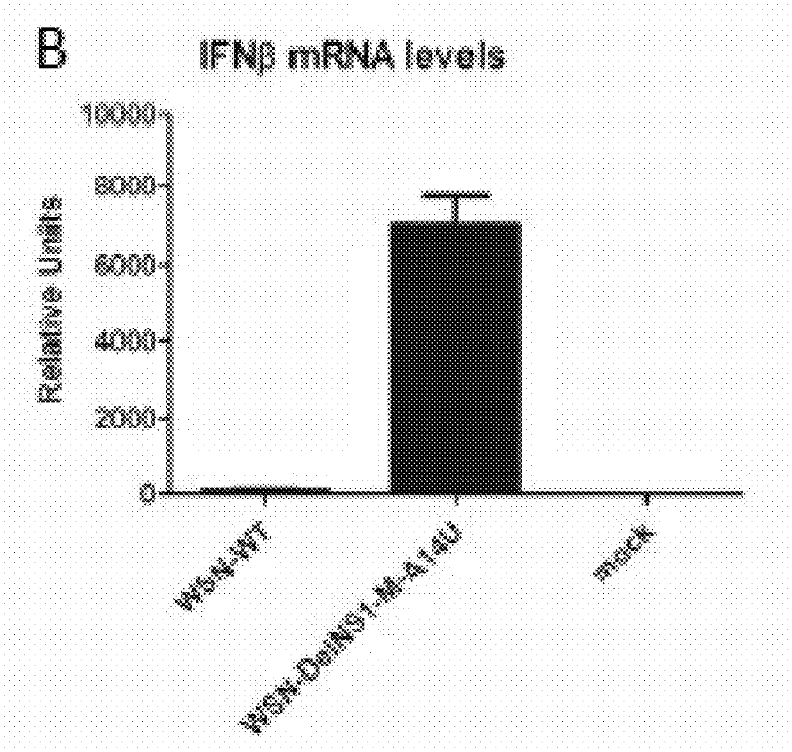
FIG. 6 is a graph showing that NS1-del virus (WSN-DelNS1-M-A14U) is not able to inhibit expression of interferon β in infected cells.

The major function of the NS1 protein is to inhibit expression of interferon in infected cells. Experiments were conducted to demonstrate that the NS1-del virus is not able to suppress host interferon expression (FIG. 6). It was particularly important to determine that the NS1-del virus has lost this function since it is associated with the virulence of the influenza virus.

Figure 7:
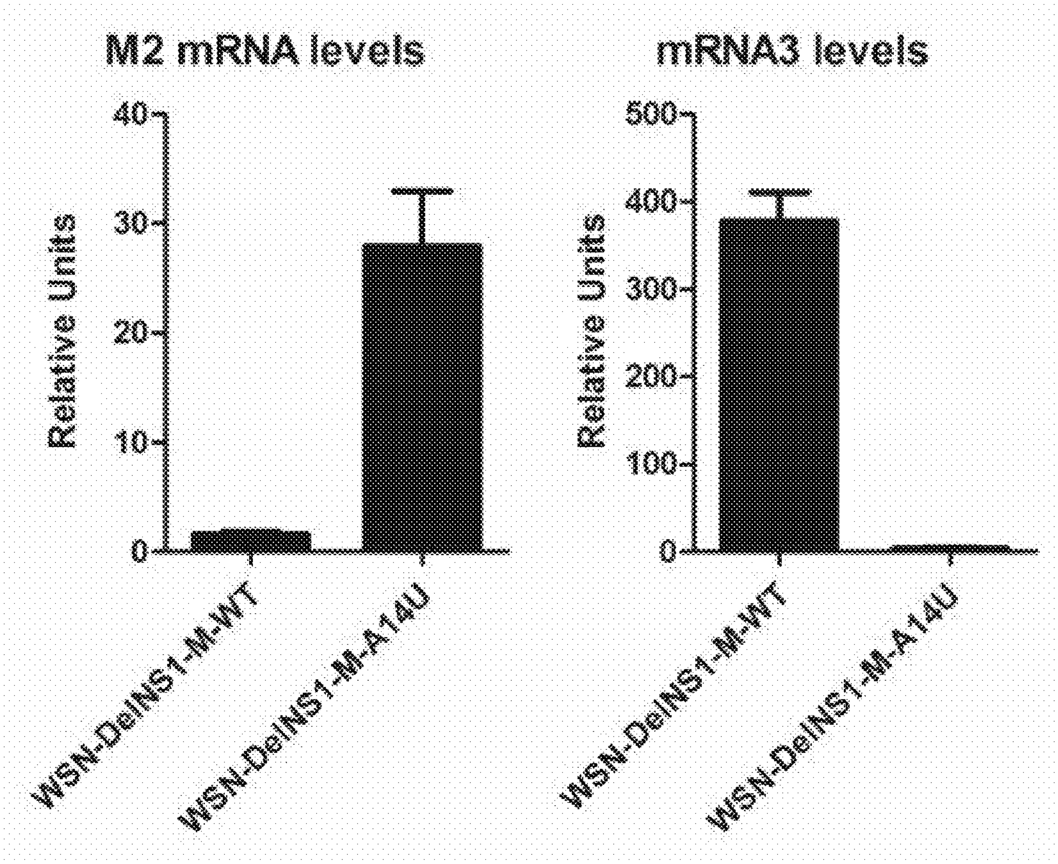
FIG. 7 show graphs indicating that mutation in the M segment of NS1-del virus (indicated as WSN-DelNS1-M-A14U) enhanced M2 but down regulated M3 transcriptions from M segment relative to wild-type M segment (indicated as WSN-DelNS1-M-WT).

Example 4—Mutation in the M Segment of the NS1-Del Virus Enhances M2 but Down Regulates M3 Transcription from the M Segment Because differential splicing of M2, M3 and M4 mRNAs play a role in the regulation of virus replication, experiments were performed that showed substitution in the M segment enhanced M2, but down regulated M3, mRNA transcription (FIG. 7). This finding offers a mechanistic explanation for the substitution of M for virus replication in the absence of NS1 protein.

Example 5—Characterization of the NS1-Del Virus in Mice

Figure 8:
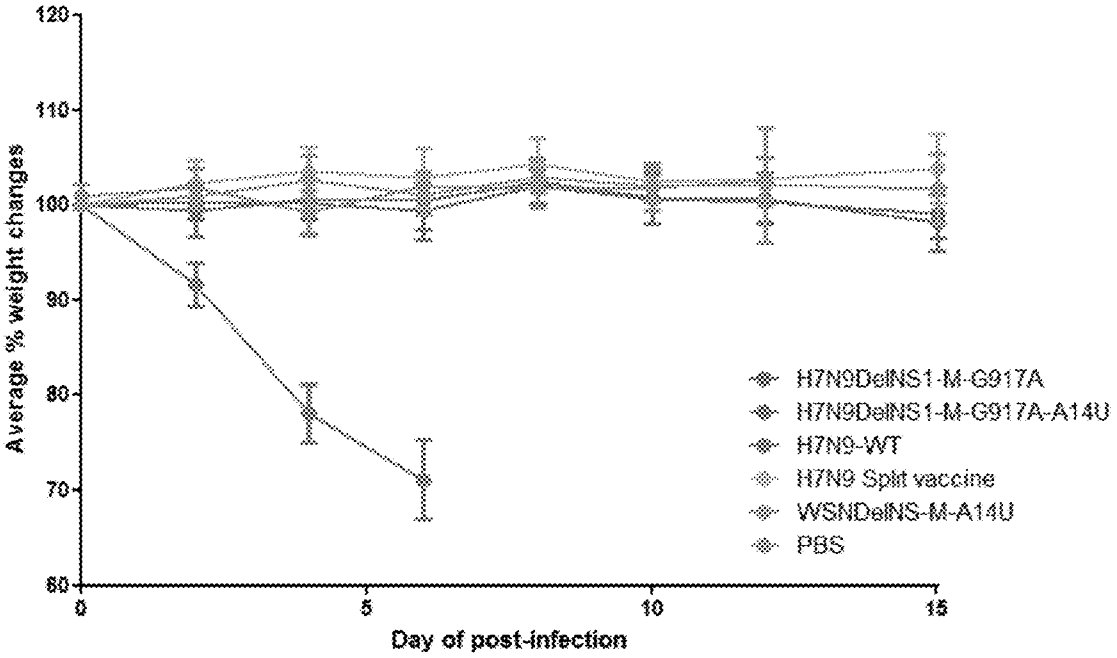
FIG. 8 shows a graph of results for a pathogenicity test of NS1-del and wild type viruses in a mouse model. Groups of six mice were inoculated with inoculums of $5\times10^4$ each virus or 3 ug of split H7N9 vaccine as specified. Mice were observed daily for changes in body weight for 14 days (day 0 to day 14). Animals that lost more than 25% of their pre-infection weight were euthanized according to protocol of animal ethics and counted as fatal outcome.

To further evaluate pathogenic properties of NS1-del viruses, experiments were conducted to examine NS1-del viruses in mice. Groups of 6 mice were infected with wild type H7N9 or NS1-del viruses and mortality and body weights were recorded daily for two weeks. It was found that mice infected with NS-del viruses showed no symptoms of disease and maintained stable body weight while mice infected with wild type H7N9 virus lost body weight from day 2 post infection; all infected mice succumbed on day 6. This result demonstrated the NS1-del virus is not virulent to mice, even at a high dose (FIG. 8).

Figure 9:
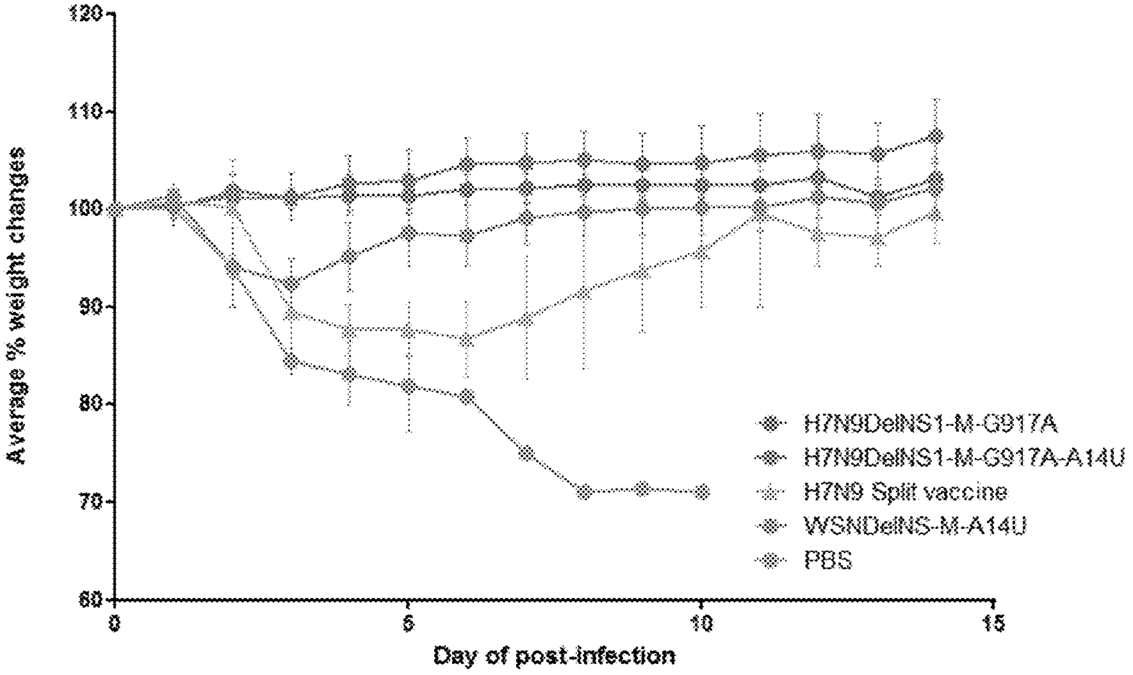
FIG. 9 shows a graph of the average % weight change in mice for the indicated days post-infection, indicating protection of mice from lethal dose challenge of H7N9 virus with vaccination of NS1-del vaccine. Mice that survived from the experiment shown in FIG. 8 were then challenged with $1\times10^5$ pfu of H7N9 WT virus. Mice were observed daily for changes in body weight for 14 days (day 0 to day 14). Animals that lost more than 25% of their pre-infection weight were euthanized according to the protocol of animal ethics and counted as fatal outcome. All mice inoculated with PBS died by day 10 of experiment after challenge of H7N9 virus. Mice inoculated with split vaccine showed significant body weight loss but were able to recover from infection. Mice inoculated with WSN-delNSA-M-A14U showed slightly decreased of body weight at the beginning of infection and recovered rapidly. No symptom or body weight loss was observed among mice inoculated with H7N9-delNS1-M-G917A or H7N9-delNS1-M-G917A-A14U after challenge with WT H7N9 virus.

Example 6—Protection of Mice from Lethal Challenge Via Immunization of NS1-Del Virus To test efficacy of an NS1-del vaccine in mice, experiments were conducted as illustrated in FIG. 9. Groups of 6 mice were first inoculated with $5\times10^4$ plaque forming units (pfu) of either various versions of NS-del viruses, a split vaccine, or PBS control. Two weeks later, mice were challenged with $10^5$ pfu of wild type H7N9 virus. Mice were monitored for mortality, and body weights were recorded for 14 days. The results in FIG. 9 showed: (1) mice inoculated with PBS control lost body weights from day 3 post infection and all mice succumbed on day 10 post challenge; (2) mice inoculated with H7N9 NS1-del viruses showed no apparent body weight loss throughout the experiment; (3) mice inoculated with H1N1 NS1-del virus showed slight body weight loss during the first four days of infection but recovered after that and stayed normally throughout rest of the experiment; (4) mice inoculated with one dose of split H7N9 vaccine showed significant body weight loss for the first week, but the mice were able to recover from infection and regained body weights. This experiment showed protection of mice from challenge with a lethal dose of highly pathogenic H7N9 virus. The NS1-del vaccine provides better protection than the split vaccine. Protection of mice from H7N9 challenge by NS1-del H1N1 virus further suggest the NS1-del vaccine may render cross protection for hetero-subtype virus infection.

Example 7—Cross Protection of NS1-Del Vaccines to Lethal Challenge with Avian H5N1 Virus Experiments to verify cross protection of DelNS1 vaccines to lethal challenge with highly pathogenic avian H5N1 virus were conducted. Besides DelNS1 virus derived from WSN and H7N9 strains, DelNS1 virus from the 2009 pandemic H1N1 virus has similarly been constructed, designated as 2009H1N1-DelNS1 and evaluated for cross protection of lethal challenge by A/Vietnam/1194/04 H5N1 virus. To test if inoculation of DelNS1 virus would provide better protection to H5N1 virus infection in mice, a 2009 H1N1 cold adapted virus, designated as 2009 H1N1-Cold adapted, was used as control. The 2009 H1N1-Cold adapted virus contains wild type NS1 gene in viral genome.

Figure 10:
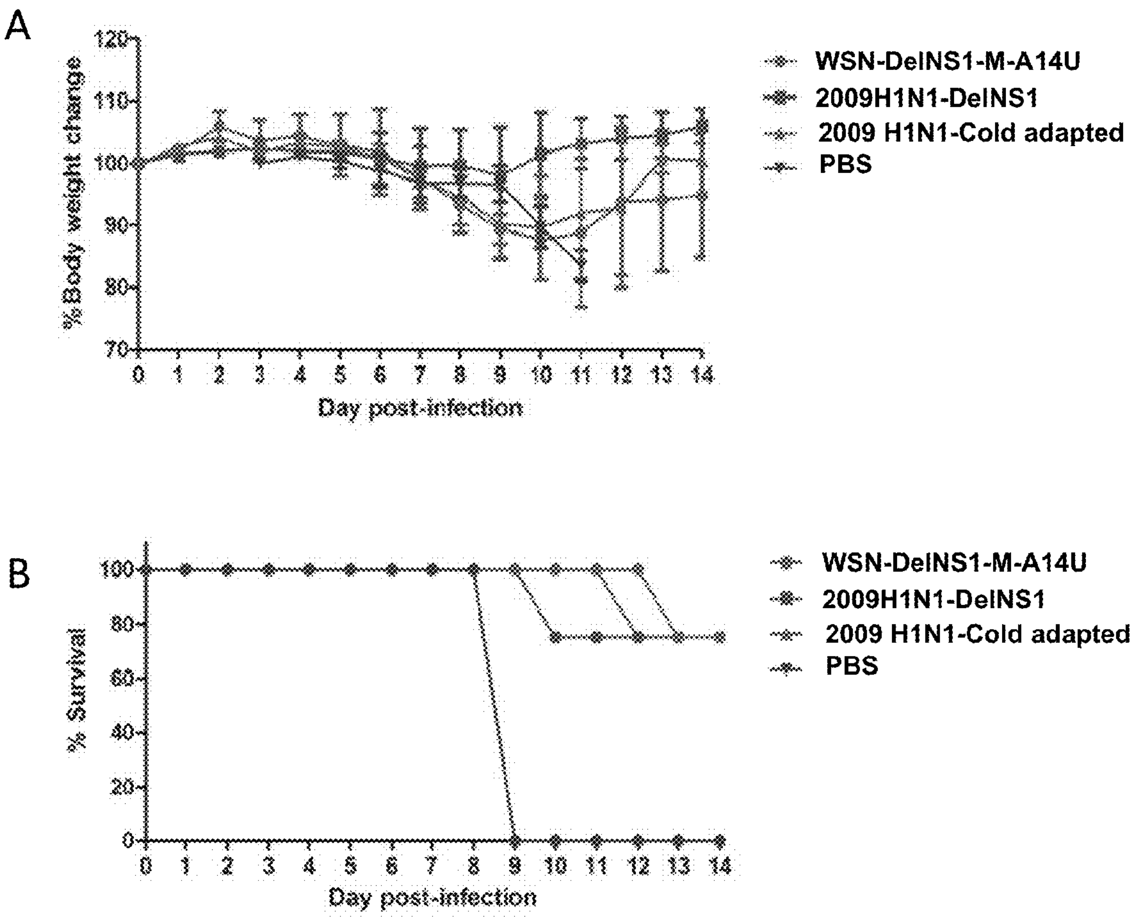
FIG. 10 shows that DelNS1 H1N1 viruses cross protect highly pathogenic avian H5N1 virus challenge. Mice were inoculated with one doses ($10^4$ PFU) of either WSN-DelNS1-M-A14U, 2009H1N1-DelNS1, 2009 H1N1-cold adapted virus, or mock inoculated with PBS for two weeks and then challenged with 100 $MLD_{50}$ of A/Vietnam/1194/04 H5N1 virus. Body weight loss (A) and (B) survival rate of mice were recorded for 14 days post H5N1 virus challenge.
Figure 11:
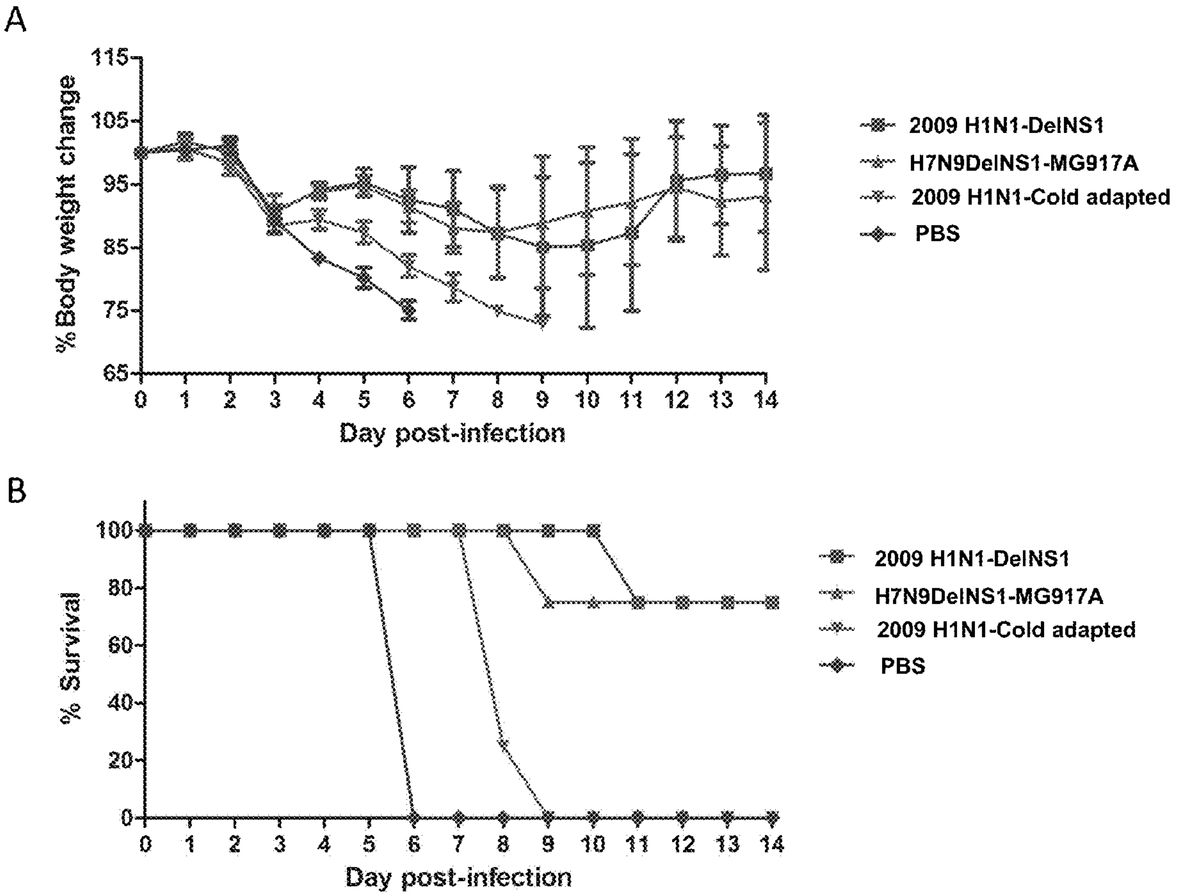
FIG. 11 shows DelNS1 live attenuated vaccines provide better cross protection than cold-adapted vaccine to high doses challenge of H5N1 virus. Mice were inoculated with one dose ($10^4$ PFU) of either 2009H1N1-DelNS1, H7N9De3NS1-G917A, 2009 H1N1-cold adapted virus, or mock inoculated with PBS, for two weeks and then challenged with 1000 $MLD_{50}$ of A/Vietnam/1194/04 H5N1 virus. Body weight loss (A) and (B) survival rate of mice were recorded for 14 days post H5N1 virus challenge.

As shown in FIG. 10, although there is some body weight lost in the beginning of infection (A), 80% of mice inoculated with WSN-DelNS1, 2009H1N1-DelNS1 and 2009 H1N1-Cold adapted viruses survived challenge of 1194 H5N1 virus at lower lethal doses (100 $MLD_{50}$). This result indicated inoculation with either cold-adapted or DelNS1 virus would provide cross protection to herterosubtypic virus infection. However, the 2009H1N1-DelNS1 virus appears to render better protection compared to the same live attenuated virus containing wild type NS1 gene based on body weight change after virus challenge (A). To further differentiate level of protection between vaccine strains containing NS1 and DelNS1, protection in mice challenged with higher lethal dose (1000 $MLD_{50}$) of A/Vietnam/1194/04 H5N1 virus was evaluated. As shown in FIG. 11, mice inoculated with PBS or the 2009 H1N1-Cold adapted virus died after 6 and 9 days post H5N1 virus challenge (A & B). However, 80% of mice inoculated either with 2009 H1N1-DelNS1 or H7N9DelNS1-MG917A virus survived the lethal challenge (B). Only less than 15% of body weight loss was observed in the beginning of infection and mice were able to recover after 10 days of H5N1 virus challenge. Taken together, these results show that DelNS1 influenza viruses provide much stronger cross protection than the vaccine strain which contains wild type NS1.

Example 8—A14U Substitution in the 3' Noncoding Region (NCR) of the M Segment of Viral RNA Supports Replication of Influenza Virus This embodiment of the invention provides that A14U Substitution in the 3' NCR of the M Segment of Viral RNA supports replication of influenza virus with an NS1 deletion by modulating alternative splicing of M segment mRNAs.

The NS1 protein of influenza virus has multiple functions and is a determinant of virulence. DelNS1 influenza virus is a useful tool for studying virus replication and can serve as effective live attenuated vaccines; however, the deletion of NS1 severely diminishes virus replication, hampering functional studies and vaccine production. The invention provides that WSN-DelNS1 viruses passaged in cells consistently adapted to gain an A14U substitution in the 3' NCR of the M segment of viral RNA (vRNA) which restored replicative ability. DelNS1-M-A14U viruses cannot inhibit interferon expression in virus infected-cells, providing an essential model for studying virus replication in the absence of the NS1. Characterization of DelNS1-M-A14U virus showed that the lack of NS1 has no apparent effect on expression of other viral proteins, with the exception of M mRNAs. Expression of the M transcripts, M1, M2, mRNA3, and mRNA4, is regulated by alternative splicing. The A14U substitution changes the splicing donor site consensus sequence of mRNA3, altering expression of M transcripts, with M2 expression significantly increased and mRNA3 markedly suppressed in DelNS1-M-A14U, but not DelNS1-M-WT, virus-infected cells. Further analysis revealed that the A14U substitution also affects promoter function during replication of the viral genome. The M-A14U mutation increases MvRNA synthesis in DelNS1 virus infection and enhances alternative splicing of M2 mRNA in the absence of other viral proteins. The findings demonstrate that NS1 is directly involved in influenza virus replication through modulation of alternative splicing of M transcripts and provide strategic information important to construction of vaccine strains with NS1 deletions.

NS1 of influenza virus has multiple functions. Besides its role in antagonizing host antiviral activity, NS1 is also believed to be involved in regulating virus replication. The NS1 protein is a virulence determinant which inhibits both innate and adaptive immunity and live attenuated viruses with NS1 deletions show promise as effective vaccines. However, deletion of NS1 causes severe attenuation of virus replication during infection, impeding functional studies and vaccine development. A replication-competent DelNS1 virus which carries an A14U substitution in the 3' NCR of the vRNA M segment is provided. M-A14U mutation supports virus replication through modulation of alternative splicing of mRNAs transcribed from the M segment. As such, the invention provides replication-competent strains with NS1 deletions which can be used as a live attenuated vaccine.

Influenza A virus is an important human respiratory tract pathogen which causes annual epidemics and occasional pandemics. The influenza A virus genome contains eight negative-sense single-stranded RNA segments. The segmented genome allows frequent reassortment events to occur between different influenza viruses, which can lead to altered pathogenic and transmission properties in reassortant viruses. The influenza A virus replication process is regulated by host and viral factors during the infection cycle. Entry of influenza virus into cells is initiated by attachment of viral hemagglutinin (HA) to cellular sialic acid receptors, which mediates an endocytotic process to release the viral genome into the cytoplasm. The viral genome is subsequently imported into the nucleus via an importin-$\alpha$1/importin-$\beta$1-dependent nuclear import pathway, where the influenza virus utilizes genome-bound viral RNP polymerase complex and host transcription machinery to replicate the viral genome and express viral mRNA for protein synthesis. At least 14 viral proteins have been identified from virus-infected cells. Among these viral proteins, PB1, PB2, PA, NP, HA, NA, M1, M2, NS1, and NS2 (NEP) are regularly expressed in infected cells. Expression of PB1-F2, PB1-N40, and PA-X is less consistently observed and may be associated with viral strain and infection conditions. Expression of an M2-related protein, M42, was also reported during infection with virus mutated at the mRNA4 splice donor site in the M segment transcript. However, many influenza A virions may fail to express at least one essential viral protein and become replication-incompetent infectious particles. Expression of viral proteins is subject to both viral and host controls and differential regulation of viral protein expression may result in differences in the replication efficiency of virus, leading to variable pathogenic outcomes of an infection.

Among the eight genome segments of influenza A virus, both the NS and M segments express differentially spliced transcripts. Two matured mRNAs, NS1 and NS2 (NEP), and four mRNAs, M1, M2, M3, and M4, are expressed from the NS and M segments, respectively. While there are four differentially spliced transcripts from the M segment, only the matrix (M1) and ion channel (M2) proteins have known roles in influenza A infection. M1 and M2 have essential functions in viral nuclear export, virion packaging, and budding during virus replication. No known function has been found for the other two mRNAs derived from the M segment, mRNA3 and mRNA4. A study of viral mRNA kinetics found that accumulation of M1 and M2 mRNA is regulated during virus infection of cells. A similar phenomenon is also observed in NS1 and NS2 (NEP) splicing regulation, which is coordinated with the progress of virus infection. The viral polymerase complex regulates the utilization of alternative 5' splice sites in influenza virus M1 mRNA, in coordination with the cellular splicing factor SF2/ASF, to control the expression of M2 mRNA during virus replication. However, another study showed that the NS1 protein regulates splicing of M segment mRNAs and that this activity requires NS1 to possess RNA binding function. Adaptive substitutions were reported to be gained in the M segment through passage of a reassortant virus containing H5 and N1 from A/turkey/Turkey/1/05 and the remaining segments from the A/PR/8/34 strain, but with NS1 deleted. While the specific functions of these M segment substitutions were not characterized, the studies seem to suggest that there is an interaction between NS1 and M functions in virus replication. Although the NS1 protein is not essential for viral replication, it has multiple functions, and deletion of the NS1 gene leads to severe attenuation of influenza virus replication. The attenuation of DelNS1 virus may be due to a loss of ability to inhibit host expression of interferon (IFN), since virus without NS1 is able to replicate normally in interferon-deficient cells. However, several studies have shown that NS1 may also be involved in regulation of influenza virus transcription and replication through other mechanisms.

An embodiment of the invention provides DelNS1 influenza viruses derived from the A/WSN/33 and A/PR/8/34 strains. While deletion of the NS1 gene usually led to severe attenuation of viruses in interferon-competent systems, an adaptive substitution, A14U, in the 3' NCR the M segment of vRNA significantly enhances the replication of DelNS1 viruses. Also, DelNS1 viruses are unable to express sufficient amounts of M2 mRNA, probably due to the absence of NS1 function, and that the M-A14U substitution restores M2 expression.

Figure 12:
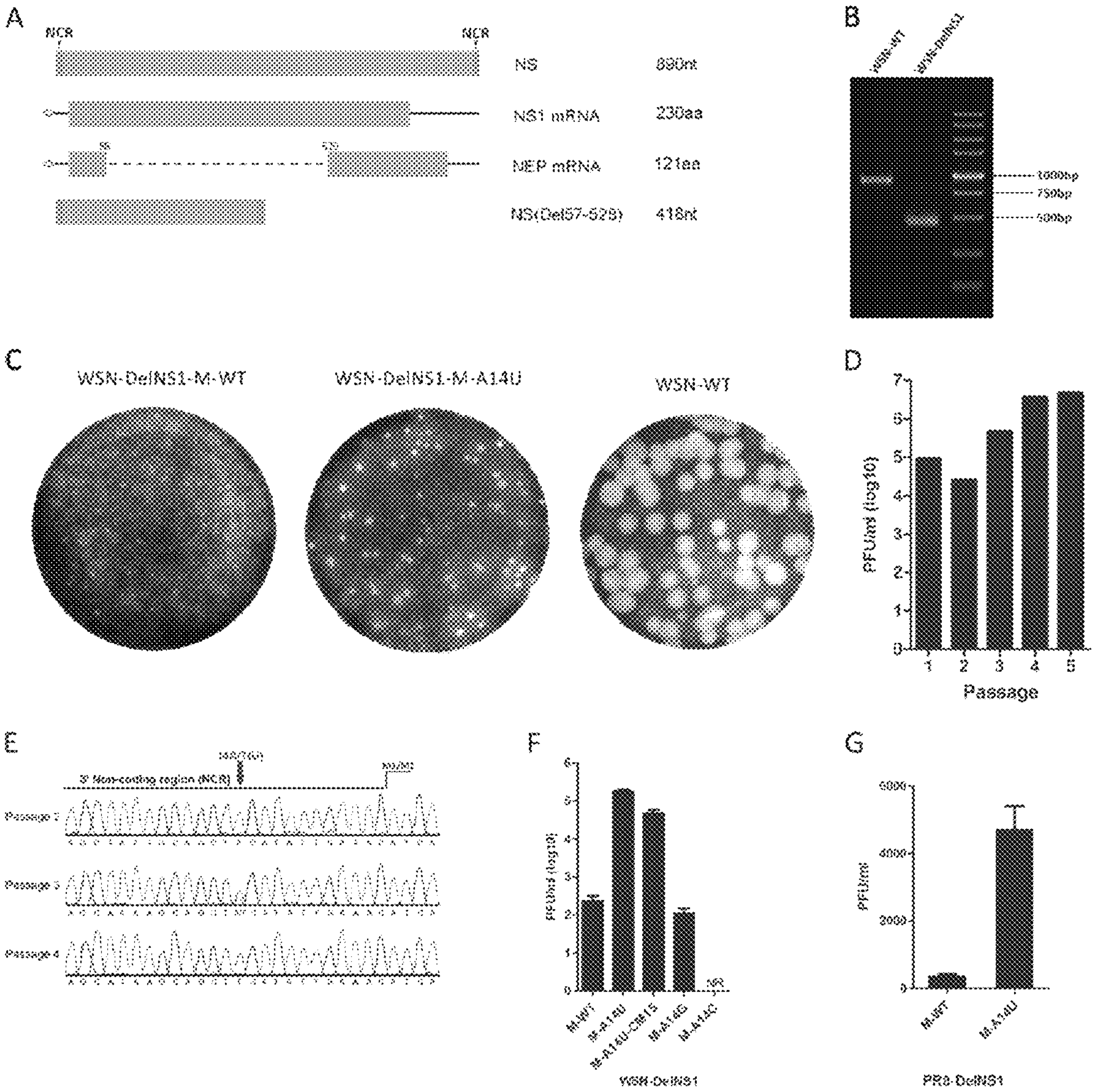
FIG. 12 shows construction and establishment of stabilized WSN-DelNS1 virus. (A) Schematic illustration of the NS segment transcripts and the NS mutant with an NS1 deletion. The DelNS1 plasmid was constructed by deleting the exon region ranging from nt 57 to 528 in the NS segment. NCR, noncoding region. (B) Confirmation of NS1 deletion in rescued DelNS1 viruses. Viral RNA was extracted from P1 virus, and the NS segment was amplified by RT-PCR and analyzed using agarose gel electrophoresis. (C) Plaque sizes of DelNS1 and wild-type A/WSN/33 viruses. (D) Titer (PFU/ml) of DelNS1 virus after each passage. (E) Sequence analysis of the DelNS1 virus genome revealed an A-to-U substitution at nucleotide position 14 in the M segment noncoding region. The noncoding region is marked by a black line, and the A14U mutation is indicated with an arrowhead. (F) Comparison of rescue efficiency for WSN-DelNS1 viruses containing M-WT and M-A14U, M-A14U-CM15, M-A14C, and M-A14G substitutions. NR, not rescued. (G) Rescue efficiency of PR8-DelNS1 viruses containing M-WT or M-A14U. The DelNS1 viruses were rescued with the indicated M-WT or M mutant plasmids in mixed HEK293T and MDCK cell cultures and then titrated by plaque assay. Values plotted are means (±standard deviations [SD]) (n=3) and are representative of data from at least 5 independent experiments.

The A14U Mutation in the Msegment is Sufficient to Restore the Growth of DelNS1 WSN Virus Although the NS1 protein of influenza virus is not essential for virus replication, viruses that do not express functional NS1 are severely attenuated and can replicate only in IFN-deficient systems. Helper viruses which express NS1 in cells have been used to support production of DelNS1 virus for vaccine studies. Substitutions in the M and NS segments have been shown to restore the growth of DelNS1 virus replication in a study using a reassortant virus containing HA and NA from an H5N1 virus and internal segments from A/PR/8/34. However, the mechanism for the restoration of growth was not defined. To better understand the role of NS1 in virus replication and to develop a method for making DelNS1 viruses, a DelNS1 version of the A/WSN/33 strain was produced (FIG. 12A). Deletion of NS1 was confirmed by examination of the viral genome.

Plaque analysis showed DelNS1 viruses form significantly smaller plaques than wild-type virus (FIGS. 12B and C). Replicative ability of the WSN-DelNS1 virus increased within three passages in MDCK cells, with the virus titer rising almost 2 logs compared to that of the original DelNS1 virus (P1) (FIG. 12D). Sequence analysis confirmed that a variant virus had been generated but found only one substitution, A14U, in the 3' NCR of the vRNA M segment (M-A14U); no other mutations were found in the genome (FIG. 12E). To confirm that introduction of M-A14U in the M segment is not a random event, the experiment was repeated and the same A14U variant was obtained. To further test whether the M-A14U mutation is sufficient to increase the growth of DelNS1 virus, efficiencies of WSN-DelNS1 virus was compared with M-WT or the M-A14U, M-A14UCM15, M-A14G, or M-A14C mutation rescued using reverse genetics and then plaque titrated the rescued viruses in MDCK cells.

A14G is biochemically similar to A14U, and the corresponding virus was also rescued, but not those with the A14C mutation. To test the potential disruption of base pairing by A14U, as it has been observed that mutations at positions 12 and 13 can affect virus growth, an M-A14U-CM15 mutant which contains an additional complementary mutation at position 15 at the 3' end of M cRNA was included. It appears that the A14U substitution is unique and requires no complementary mutation. The titer of rescued DelNS1-M-A14U mutant viruses was as high as $1.75\times10^5$ PFU/ml, about 750-fold higher than that of the M-WT DelNS1 virus (FIG. 12F). To test if the A14U substitution may also arise in other cells, WSN-DelNS1 virus was passaged in Vero cells. However, no mutation was observed after more than eight passages.

To further verify that M-A14U also supports replication of other influenza virus strains, this substitution was introduced into the M segment of a DelNS1 version of the A/PR/8/34 strain and, consistent with the observation with WSN, M-A14U significantly enhanced the titer of virus rescued (FIG. 12G), while PR8-DelNS1 virus without the M-A14U substitution could not be rescued. These results indicate that the M-14U substitution can restore virus replication in the absence of NS1 protein expression.

Figure 13:
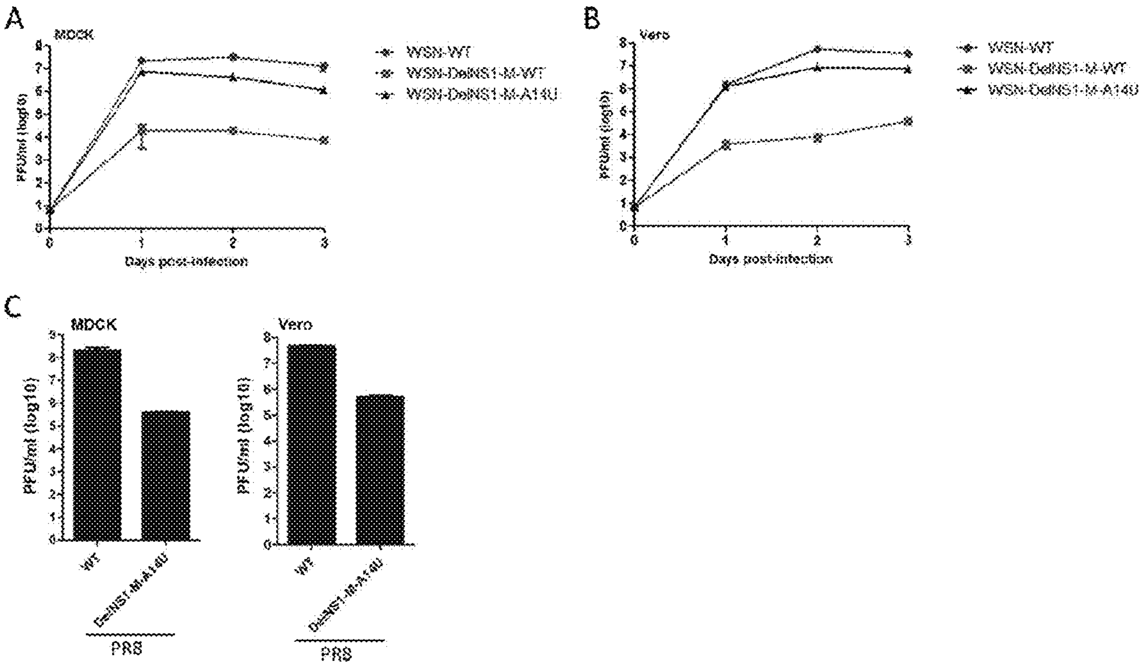
FIG. 13 shows growth kinetics of the M-A14U-DelNS1 virus in MDCK and Vero cells. (A and B) Column-purified reverse genetic WSN-WT, WSN-DelNS1-M-A14U, and WSN-DelNS1-M-WT viruses were used to infect MDCK cells (A) or Vero cells (B) at a multiplicity of infection (MOI) of 0.1. Supernatants were collected at the indicated time points and virus titrated by plaque assay. (C) Column-purified reverse genetic PR8-WT and PR8-DelNS1-M-A14U viruses were used to infect MDCK cells (left panel) and Vero cells (right panel) at an MOI of 0.1. Supernatants were collected at 24 h post-infection and titrated by plaque assay. The values (mean±SD; n=3) plotted are representative data from at least 3 independent experiments.
Figure 14:
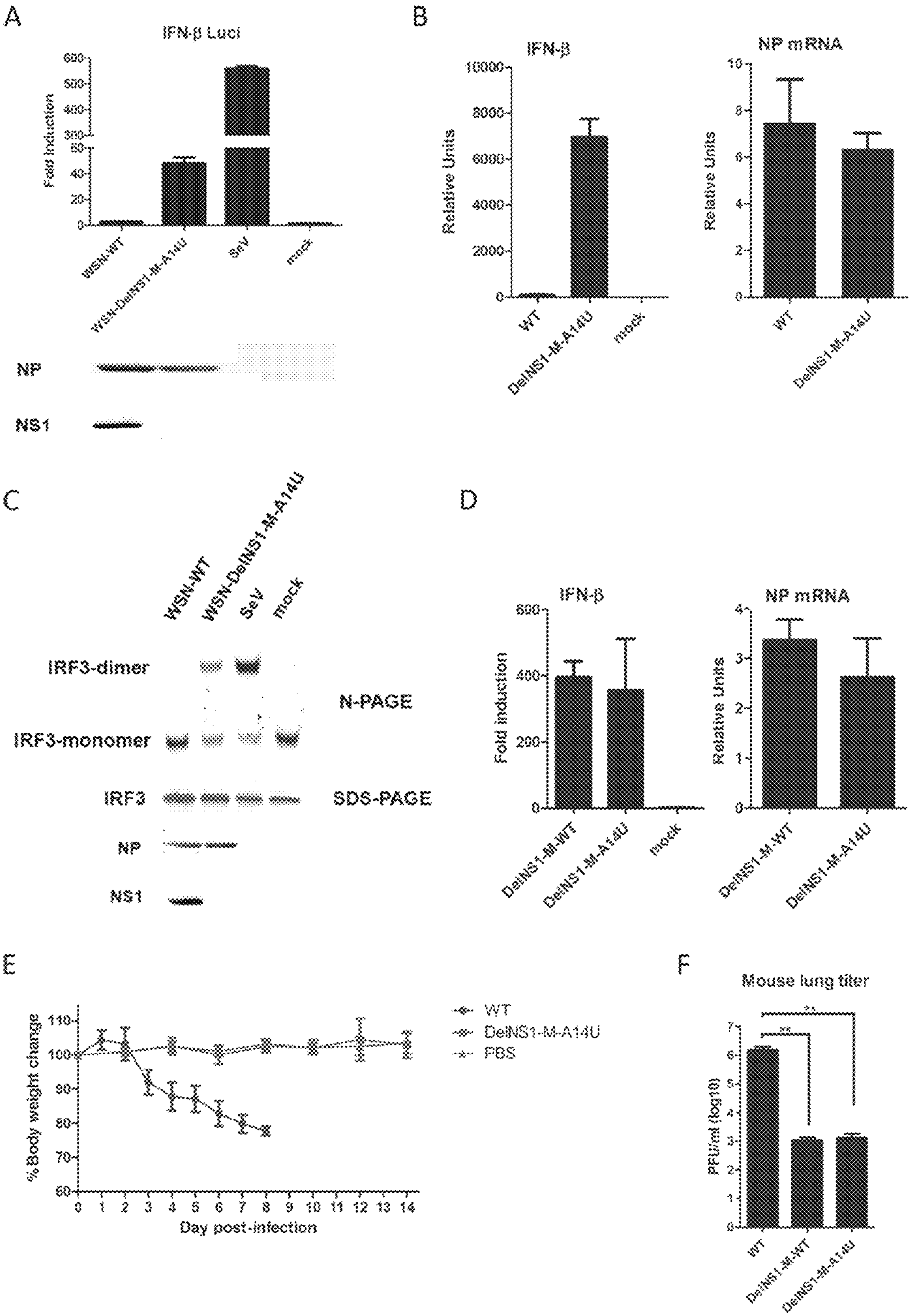
FIG. 14 shows Loss of IFN-β suppression activity in WSN-DelNS1 viruses. (A) HEK293T cells were transfected with an IFN-$^{L}$ reporter plasmid 24 h prior to infection with either WSN-WT or WSN-DelNS1-M-A14U at an MOI of 1 or with the positive control, SeV, at 50 HA units. After 24 h, cells were harvested and cell lysates prepared for estimation of luciferase activity. The luciferase assays were performed in triplicate, and values were normalized to the Renilla luciferase control. (B) IFN-β and viral NP mRNA levels were quantified by qRT-PCR after MDCK cells were infected with WSN-WT or WSN-DelNS1-M-A14U at an MOI of 0.1 and cultured for 16 h. Values were normalized against canine actin. (C) Suppression of IRF3 dimerization in HEK293T cells infected with WSN-WT, WSN-DelNS1-M-A14U, or SeV was analyzed by native gel electrophoresis. (D) Activity in suppressing IFN-β expression was compared in MDCK cells infected with WSN-DelNS1-M-WT or WSN-DelNS1-M-A14U virus. Similar to the experiment described for panel B, MDCK cells were infected with the indicated viruses at an MOI of 0.1, and at 16 h postinfection, IFN-β and NP mRNA levels were quantified by qPCR. Values were normalized to canine actin. (E) Groups of six BALB/c mice, aged 6 to 8 weeks, were intranasally inoculated with $5\times10^4$ PFU of WSN-WT or WSN-DelNS1-M-A14U mutant virus, and body weight was monitored daily for 14 days post-infection. (F) Replication efficiency of viruses in lung tissues of infected mice. Groups of three mice were infected with $10^4$ PFU of WSN-WT, WSN-DelNS1-M-WT, or WSN-DelNS1-M-A14U mutant viruses and then euthanized at 72 h post-infection, with lung tissues from each mouse being collected and homogenized for virus titration by plaque assay using MDCK cells. Statistical significance was analyzed by one-way analysis of variance (ANOVA) or Student's t test (**, p<0.01). The bars plotted show means±SD (n=3), and the results represent at least three independent experiments.

The M-A14U Substitution Supports Virus Replication but does not Suppress IFN Expression DelNS1 influenza virus is unable to replicate in MDCK cells and can be grown only in Vero cells. Analysis of growth kinetics showed that M-A14U DelNS1 virus is able to replicate to a titer comparable to that of the wild-type virus (less than one log lower) in both MDCK and Vero cells (FIGS. 13A and B). Similarly, the M-A14U substitution supports PR8 DelNS1 virus replication in Vero and MDCK cells, while PR8 DelNS1 virus without this substitution cannot be propagated (FIG. 13C). The function of the NS1 protein as a viral antagonist of host antiviral activity is well defined. Deletion of NS1 attenuates virus ability to suppress interferon expression, as measured in a reporter assay and by qRT-PCR of IFN-β activation (FIGS. 14A and B). The DelNS1-M-A14U virus is unable to suppress activation of IRF3 in infected cells (FIG. 14C). While M-A14U enables DelNS1 virus to grow more efficiently than WSN-DelNS1-M-WT virus, this substitution has no effect on suppression of interferon (FIG. 14D). To further determine if the A14U substitution in the M segment may alter the pathogenic properties of virus in vivo, the virulence and replication was compared in lung tissues of WSN-WT and WSN-DelNS1-M-A14U mutant viruses in mice. While wild-type WSN strains cause rapid body weight loss and death in infected mice, no apparent pathogenicity was observed with WSN-DelNS1-M-A14U mutant viruses. Estimation of viral titers in the lung tissues of infected mice shows that both WSN-DelNS1-M-A14U and WSN-DelNS1-M-WT mutants replicate poorly in lung tissues, to levels approximately 3 logs lower than are observed for WSN-WT virus (FIGS. 14E and F). Thus, introduction of the M-A14U substitution retain the avirulent properties possessed by DelNS1 virus which make it suitable for use in vaccine development.

The M-A14U substitution affects splicing of M transcripts in virus replication. The NS1 protein is not a component of the viral polymerase complex. The observation that a sole A14U substitution in the M segment restores replication in DelNS1 virus suggests that NS1 may be involved in regulating replication or transcription from the vRNA M segment. To understand the molecular basis for the role of the M-A14U substitution in supporting replication of virus with an NS1 deletion, the expression of virus proteins during infection of MDCK cells with DelNS1-M-A14U virus was examined. While the expression pattern of viral HA and NP proteins is largely similar in WSN-WT and DelNS1-MA14U virus infections (FIG. 15A), M2 expression was unchanged and M1 levels were significantly decreased in M-A14U DelNS1 compared to WSN-WT virus infections. Comparison of viral protein expression between DelNS1-M-A14U and DelNS1-M-WT viruses also showed that the A14U substitution had an effect on the M1 and M2 proteins but not on HA and NP (FIG. 15B). However, the enhancement effect of the M-A14U substitution on M2 protein expression is not apparent in WSN virus with intact NS1 function (FIG. 15C), suggesting that M-A14U may be essential for compensation of the loss of NS1 functions in regulation of expression and splicing of M mRNAs.

The M-A14U mutation elevates expression of M2 mRNA through downregulation of mRNA3 during virus replication. During M segment transcription, differential splicing occurs to generate four transcripts, with M1 and M2 mRNAs expressing M1 and M2 proteins, respectively, during influenza virus infection (FIG. 15A). The function of mRNA3 and mRNA4 is unknown. Notably, the A14U mutation is located in the mRNA3 splicing consensus sequence, which covers nucleotides (nt) 9 to 17 at the 5' end of the noncoding region of M mRNAs. The A14U substitution may alter the splicing donor (SD) site consensus sequence of mRNA3 from CAG/GUA to CAG/GUU and affects production of mRNA3. Also, the A14U substitution in the vRNA M segment may support DelNS1 virus growth by downregulating mRNA3 expression to increase the ratio of M2 to M1 mRNA expression.

To verify this hypothesis, qRT-PCR analysis was used to examine mRNA3 levels in virus-infected cells. As expected, among the four M mRNA transcripts, M1, M2, and M4 were significantly increased but mRNA3 was almost completely abolished in WSN-DelNS1-MA14U virus-infectedMDCK-cells (FIG. 16B). In contrast, the expression of NPmRNA was not affected by M-A14U substitution in DelNS1 viruses (FIG. 16B), suggesting that deletion of NS1 is specifically associated with regulation of expression from the M segment.

Further, HEK293T cells were transfected with either M-A14U or M-WT segment plasmids which express full-length M mRNA. While levels of M1 mRNA are similar for M-WT and M-A14U plasmids, expression of mRNA3 is markedly downregulated and that of M2 mRNA is significantly upregulated from the M-A14U plasmid (FIG. 16C). Coexpression of NS1 further demonstrated the positive effect of NS1 on transcription of M mRNAs; the A14U substitution may have arisen in the DelNS1 virus to compensate for the NS1-associated enhancement of M mRNA expression. The M-A14U substitution has a similar effect in supporting replication of DelNS1 virus derived from the A/PR/8/34 strain (FIGS. 12G and 13C). Examination of differentially spliced M transcripts from PR8-DelNS1-M-A14U virus-infected cells found patterns similar to those observed with WSN-DelNS1-MA14U (FIG. 16D), supporting conservation of function for this nucleotide in both WSN and PR8 strains. Thus, M-A14U substitution in the vRNA M segment alters the splicing pattern of M1 mRNA during virus infection, even in the absence of other viral proteins.

The M-A14U Mutation Results in an Increased Ratio of M2 mRNA to M1 mRNA

Figure 15:
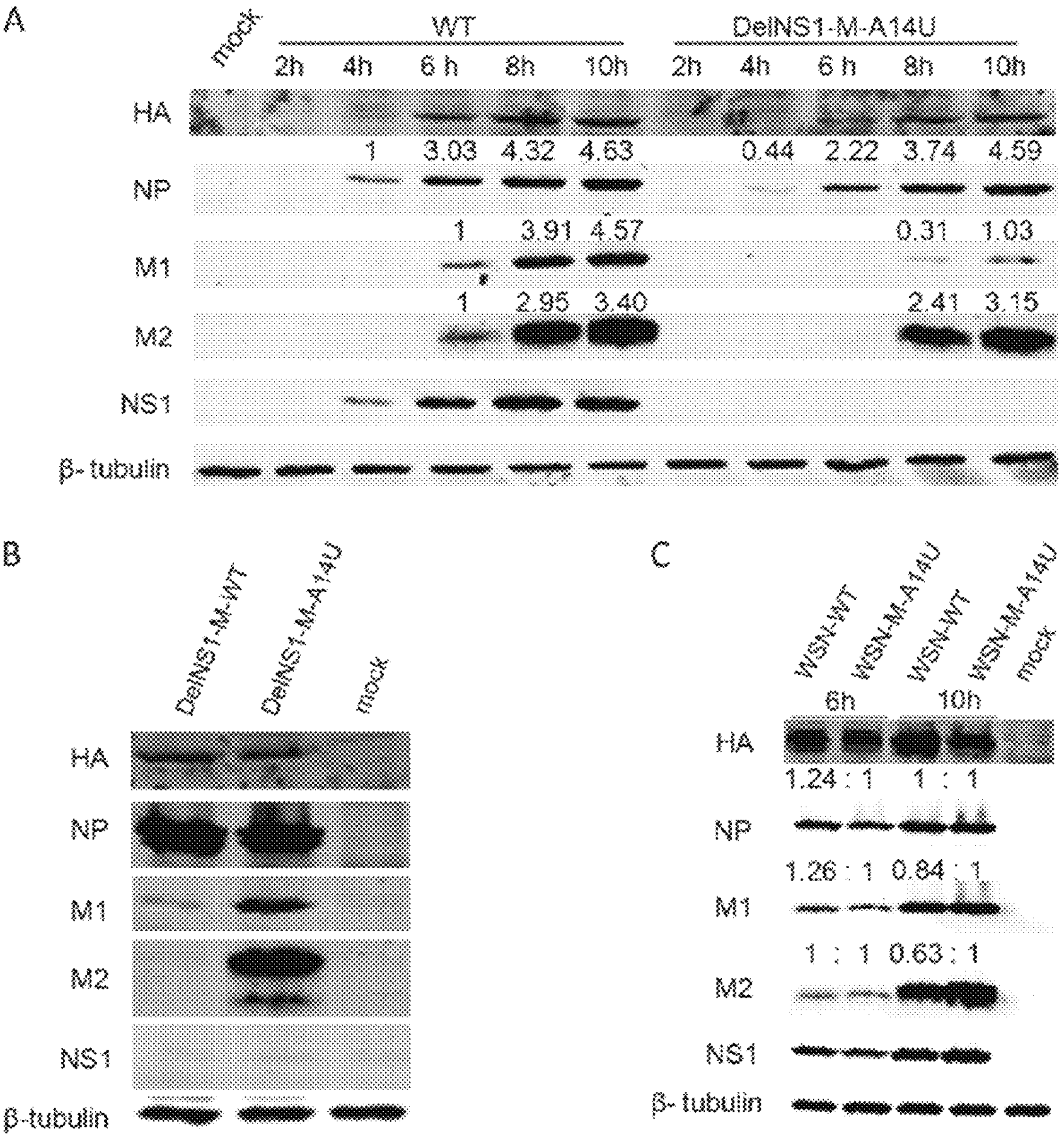
FIG. 15 shows the effect of M-A14U mutation on M1 and M2 protein expression. (A) MDCK cells were infected with WSN-WT or WSN-DelNS1-M-A14U virus at an MOI of 2. Cells were harvested at the indicated time points and cell lysates analyzed by Western blotting with specific antibodies, as described in Materials and Methods. (B) MDCK cells were infected with WSN-DelNS1-M-WT or WSN-DelNS1-M-A14U virus at an MOI of 0.1. At 16 h postinfection, cell lysates were collected for Western blotting with specific antibodies. (C) MDCK cells were infected with WSN-WT or WSN-M-A14U virus at an MOI of 5. Cell lysates were prepared at the indicated time points for Western blotting with specific antibodies. β-Tubulin was included as a loading control. All of the results are representative of three independent experiments.
Figure 16:
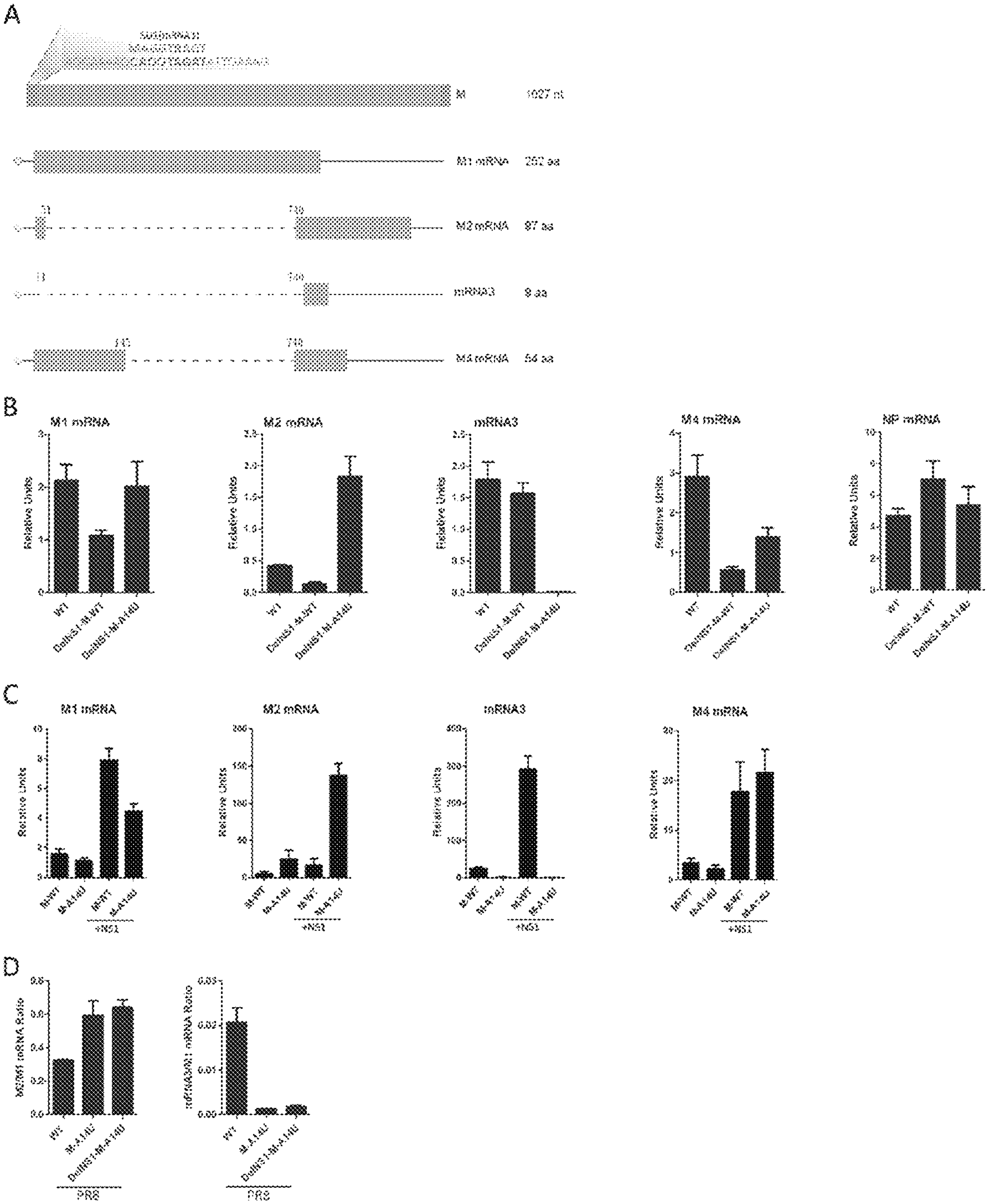
FIG. 16 shows the effect of M-A14U substitution on alternative splicing of M transcripts. (A) Schematic illustration of the M segment transcripts. The sequence of the 3' NCR of the vRNA M segment is shown in red, with the mRNA3 splicing donor (SD) site highlighted in yellow. Splicing consensus sequences for the donor site are indicated in green above the noncoding region sequence (M, A or C; R, A or G). (B) Analysis of levels of different M mRNAs in virus-infected cells. MDCK cells were infected with the indicated viruses at an MOI of 0.1. Total RNA was isolated at 16 h post-infection. The mRNA levels for M1, M2, mRNA3, and M4 were determined by quantitative RT-PCR, as described in Materials and Methods. (C) HEK293T cells were transfected with pHW2000-WSN-M-WT or pHW2000-WSN-M-A14U plasmid with or without cotransfection of pCX-WSN-NS1 for coexpression of NS1. At 48 h post-transfection, total RNAs were isolated. After DNase treatment, the mRNA levels were determined by quantitative RT-PCR. (D) MDCK cells were infected with PR8-WT, PR8-M-A14U, or PR8-DelNS1-M-A14U virus at an MOI of 0.1. At 16 h post-infection, total RNAs were isolated and mRNA levels measured by qPCR. M2/M1 mRNA and mRNA3/M1 mRNA ratios are shown. All the results plotted indicate means±SD (n=3) and are representative of three independent experiments.
Figure 17:
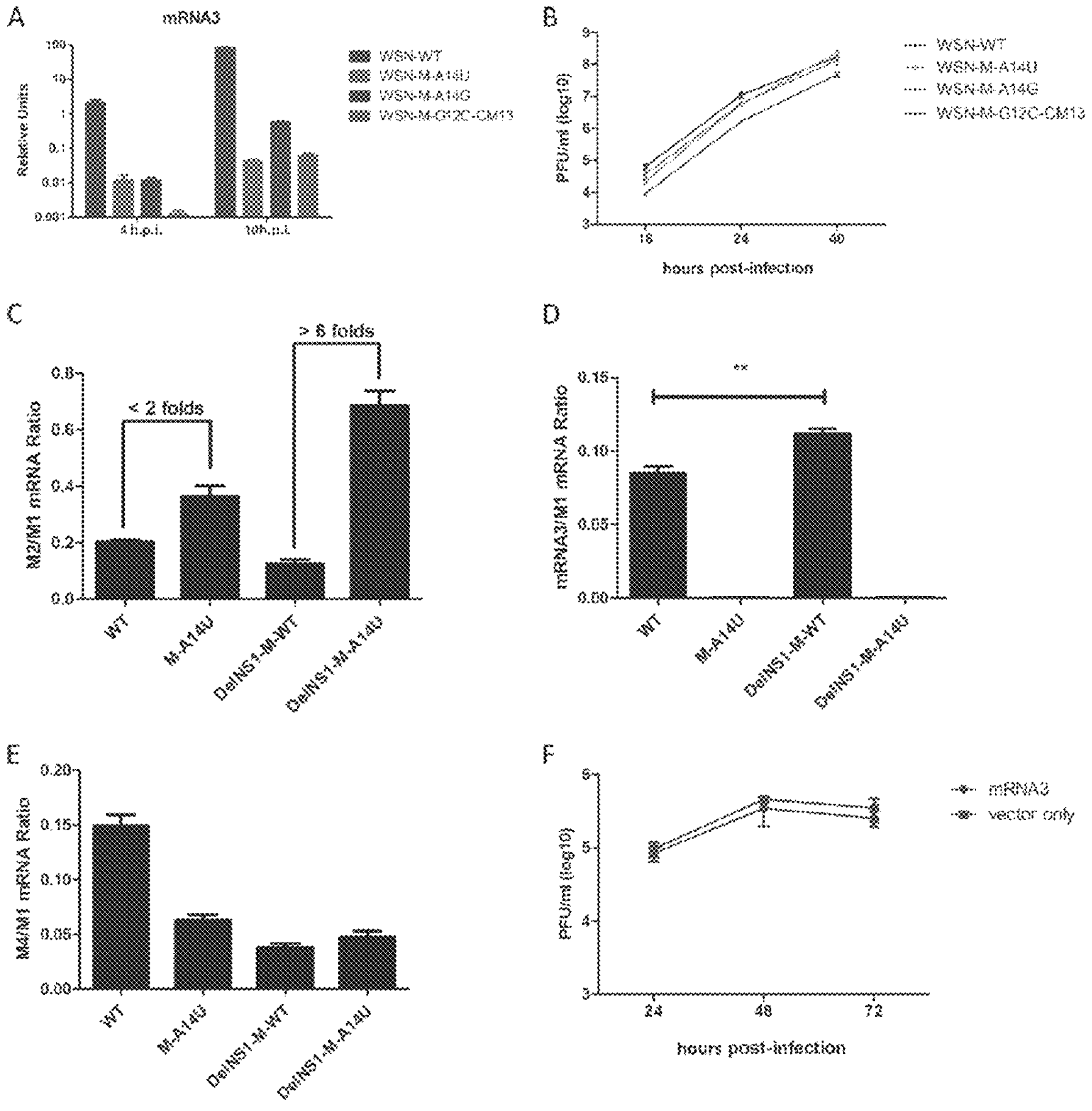
FIG. 17 shows the effect of M-A14U substitution on M2/M1 mRNA ratio. (A) MDCK cells were infected with WSN-WT, WSN-M-A14U, WSN-M-A14G, or WSN-MG12C-CM13 virus at an MOI of 5. Total RNAs were extracted at the indicated time points and levels of mRNA3 determined by quantitative RT-PCR. (B) Analysis of growth kinetics of WSN-WT, WSN-M-A14U, WSN-M-A14G, and WSN-M-G12C-CM13 viruses. MDCK cells were infected with these viruses at an MOI of 0.001. Supernatants were collected at the indicated time points and titrated by plaque assay. (C to E) MDCK cells were infected with WSN-WT, WSN-M-A14U, WSN-DelNS1-M-WT, or WSN-DelNS1-M-A14U virus at an MOI of 0.1. At 16 h after infection, total RNAs were isolated, and the M2/M1, mRNA3/M1, and M4/M1 mRNA ratios were determined by quantitative RT-PCR. (F) Effect of mRNA3 on virus replication. HEK293T cells were transfected with pCX-WSNmRNA3 or a control vector 24 h prior to infection with WSN-DelNS1-M-A14U virus at an MOI of 0.1. Supernatants were collected at the indicated time points and virus titrated by plaque assay. All of the bars and points plotted indicate means±SD (n=3) from three independent experiments. **, p=0.0013 by Student's t test.

To further explore the molecular mechanism underlying the effects of M-A14U on virus replication in the absence of NS1 expression, mutants were made which downregulate the expression of mRNA3. The M-G12C-CM13 mutant virus markedly downregulates the expression of mRNA3. Also, the expression of mRNA3 is reduced in WSN-MA14U, WSN-M-A14G, and WSN-MG12C-CM13 virus infection (FIG. 17A). However, growth kinetics analysis showed that replication of this virus is attenuated, with the WSN-DelNS1-M-G12CCM13 virus unable to be efficiently rescued (FIG. 17B) suggesting that downregulation of mRNA3 may not be directly associated with virus growth. The M1 matrix protein is involved in vRNA nuclear export, while M2 has an ion channel function and is involved in the virus uncoating and budding process during influenza virus replication. There may be a coordination of expression of M1 and M2 over the course of the viral replication through regulation of alternative splicing of M1 mRNA and that NS1 may play also a role in this. The ratio of M1 to M2 may be altered in DelNS1 virus infection, as seen in the above (FIGS. 15 and 16). M2 is reported to be selectively expressed during the early hours of virus infection, which suggests a critical role for M2 in the early phase of virus replication. In addition to its role in the virus uncoating and budding process, M2 is reported to interact with autophagosomes and inflammasomes, suggesting that it plays other roles during virus replication. In the absence of NS1, which has multiple functions to antagonize host antiviral activities, DelNS1 viruses may adapt to preferentially express M2 in an attempt to maintain an optimal balance for virus replication.

To understand the effect of M-A14U on regulation of differential splicing of M transcripts, the ratio of M2 mRNA to M1 mRNA in virus-infected cells was determined. The M2/M1 ratios was compared in cells infected with WSN-M-A14U, WSN-DelNS1-M-WT, WSNDelNS1-M-A14U, and WT WSN viruses. The M2/M1 splicing efficiency in WSN-DelNS1-M-A14U-infected cells was about 6-fold higher than that in WSN-DelNS1-M-WT-infected cells (FIG. 17C). However, comparison between WSN-WT and WSN-M-A14U M2/M1 ratios revealed that while M2 is upregulated with the A14U substitution, the effect is not as significant (less than a 2-fold difference) as that seen between the WSN-DelNS1 viruses (FIG. 17C). Expression of mRNA3 is diminished and M4 mRNA is downregulated in both WSN-WT-M-A14U and WSNDelNS1-M-A14U virus infections (FIGS. 17D and E).

To further test the effect of mRNA3 on virus growth, mRNA3 was expressed from a plasmid, but no negative effect was observed on virus titers (FIG. 17F), which suggests that alternative splicing for expression of mRNA3 may be solely for modulating the levels of M1 and M2 mRNAs. These results support the hypothesis that M-A14U mutation leads to increased alternative splicing for production of M2, and perhaps also M1, mRNAs to enhance virus replication in the absence of NS1 expression.

The M-A14U Mutation Enhances Alternative Splicing of M2 mRNAs and Synthesis of M vRNA Previous studies have suggested that splicing of M segment mRNAs can be regulated by the viral RNP complex, in conjunction with the host factor SF2 or NS1. These mechanisms may be associated with the M-A14U substitution. The M-A14U substitution affects splicing efficiency of M1 mRNA and that this property is required to compensate for lack of NS1 expression. In a mechanism where NS1 is involved in the regulation of splicing of M transcripts into M2 mRNA during virus replication, it seems possible that DelNS1 virus may be forced to obtain an adaptive substitution in the regulatory element at the promoter region of the vRNA M segment which normally associates with NS1 in order to compensate for a lack of NS1 function.

Figure 18:
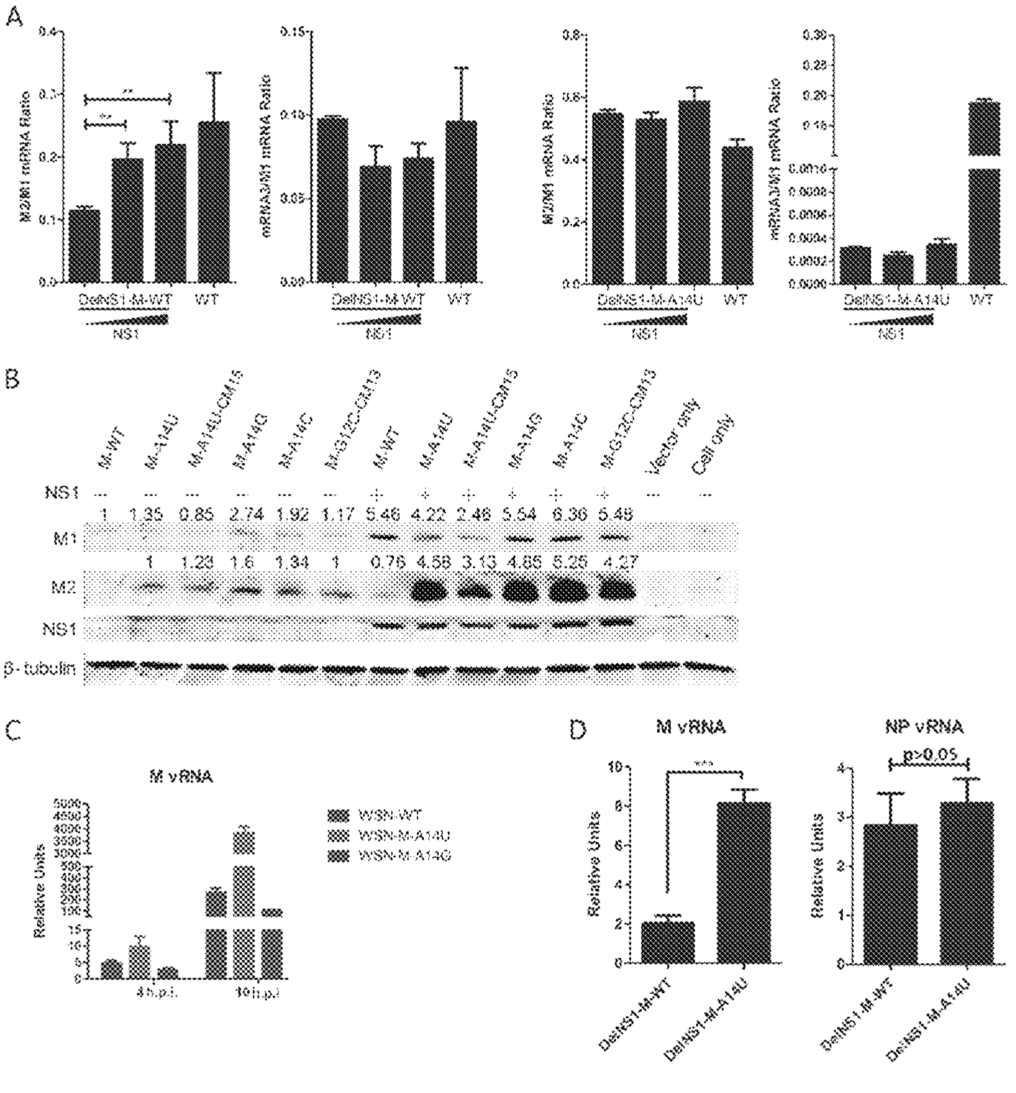
FIG. 18 shows Regulation of M mRNA splicing host machinery by viral NS1 and polymerase proteins. (A) HEK293T cells were transfected with increasing amounts of pCX-WSN-NS1. At 24 h after transfection, cells were infected with WSN-DelNS1-M-WT, WSN-DelNS1-M-A14U, or WSN-WT virus at an MOI of 0.5. Total RNAs were isolated at 8 h post-infection and M1 mRNA, M2 mRNA, and mRNA3 levels analyzed by quantitative RT-PCR. (B) HEK293T cells were transfected with WT and various mutants of the M segment cloned into pHW2000 plasmids, which express M vRNA, with or without the pCX-WSN-NS1 plasmid. Cell lysates were prepared at 48 h post-transfection for Western blotting with specific antibodies. β-Tubulin was included as a loading control. (C) Effect of A14U substitution on M vRNA replication. MDCK cells were infected with WSN-WT, WSN-M-A14U, or WSN-M-A14G virus at an MOI of 5. At 4 and 10 h post-infection, total RNAs were isolated for qRT-PCR analysis, and relative amounts of vRNA were determined as described above. (D) The A14U substitution enhances MvRNA replication. MDCK cells were infected with WSN-DelNS1-M-WT or WSN-DelNS1-M-A14U virus at an MOI of 0.1. Total RNAs were isolated at 16 h after infection. M and NP vRNA levels were determined by quantitative RT-PCR, as described above. All bars plotted show means±SD (n=3). The results represent three independent experiments. , p<0.01; *, p=0.0002 (by Student's t test).

To test this hypothesis, the effect of restoring NS1 expression on the M2/M1 ratio was examined in DelNS1-M-WT virus-infected cells. Increasing amounts of NS1 expression vector were transfected into HEK293T cells 24 h prior to infection with virus, and expression of M1 and M2 viral mRNAs was estimated by quantitative RT-PCR. The amount of the M2 spliced form rises as levels of NS1 expression increase in DelNS1-M-WT virus-infected cells (FIG. 18A). Using plasmids which express both the vRNA and mRNA of the M segment, it was observed that even in the absence of other viral proteins, all plasmids with substitutions at position 14 expressed higher levels of M2 protein, but not M1, than M-WT, which indicates that M-A14U is associated with upregulation of the M2 spliced form (FIG. 18B). Cotransfection of NS1 plasmid M significantly enhances the expression of M1 from all of these plasmids, and levels of M2 are upregulated more significantly for plasmids which have a substitution at the $14^{th}$ position or at the $12^{th}$ position to downregulate mRNA3 (G12C-CM13) (FIGS. 17A and 18B). This result strongly suggests that NS1 can function to allow preferential expression of M1 and M2 through downregulation of the alternative splicing site for mRNA3, while substitutions at this splicing site allow efficient processing of M1 into the M2 spliced form.

The A14U substitution occurs in the 3' noncoding region of the M vRNA segment (5' of cRNA or 5' mRNA), which is also the promoter region for replication of the viral genome. This mutation may affect the binding of the viral polymerase complex to enhance vRNA synthesis from the M segment, producing more M1 mRNA for splicing into M2 mRNA during virus replication. M vRNA synthesis levels in cells infected with mutant viruses containing variations at position 14 and with an intact NS1 gene was tested. The level of M vRNA produced from the WSN-M-A14U mutant was approximately 15-fold higher than that for WSN-WT virus (FIG. 18C). In contrast, relatively lower levels of M vRNA were observed for the WSN-M-A14G mutant than for WSN-WTvirus-infected cells (FIG. 18C).

Whether elevated production of M vRNA is associated with DelNS1-MA14U virus infection was tested. The levels of M vRNA are significantly higher in WSN-DelNS1-M-A14U than in WSNDelNS1-M-WT virus infections, while no similar trend is observed for NP vRNA (FIG. 18D). Thus, M-A14U mutation positively affects M vRNA synthesis and that this effect may be required for replication of NS1-deficient viruses.

Influenza virus utilizes the viral polymerase complex and host machinery to transcribe and replicate the viral genome in the nucleus. Coordination of expression of viral products for switching from transcription to replication and nuclear export of vRNAs to the cytoplasm is critical for optimal replication efficiency. The viral proteins M1 and NEP (NS2) are involved in nuclear export of vRNPs. M2 is a structural protein and is involved in the virus uncoating process during the early phase of entry and virion budding in the late stage of virus infection. M1/M2 and NS1/NS2 (NEP) viral proteins are expressed through alternatively spliced mRNAs from the M and NS segments, respectively. While there is no direct involvement of proteins from the M or NS segment in the viral polymerase complex, it is suggested that virus replication can be regulated through modulation of alternative splicing of M1/M2 and NS1/NEP (NS2) mRNAs. While influenza virus utilizes viral polymerases to replicate and a cap-snatching mechanism to transcribe the viral genome, it is believed that the virus is dependent on host machinery for mRNA splicing. Expression of spliced NS and M mRNAs is highly regulated. NS1 was found to inhibit host pre-mRNA splicing through interaction with CPSF and may also have the same effect on viral mRNA.

Previous studies showed that both viral and host mechanisms are involved in the regulation of differential splicing of M mRNAs. Since M1 and M2 proteins have essential functions required for different stages of viral infection, such as RNP nuclear export, virus assembly, and budding processes, control of the timing of M1 and M2 expression to optimize efficiency of viral genome replication is critical for virus infection. The 3' NCR of the vRNA M segment contains 25 nucleotides which comprise a promoter for transcription initiation and alternative splicing sites for posttranscriptional processing of mRNA (FIG. 16A). The viral polymerase complex may be binding onto the NCR promoter region to block the splicing site for expression of mRNA3, leading to the alternative utilization of another splicing site for M2 mRNA. Another study found that it is the NS1 protein which regulates the accumulation of M2 in virus replication. However, the regulatory effect of NS1 on accumulation of M2 was not observed in Vero cells infected with DelNS1 virus.

The role of the NS1 protein in virus replication was studied by constructing an NS1 deletion virus derived from the A/WSN/33 influenza virus strain. A14U substitution in the noncoding region of the M segment arose in DelNS1 virus after a few passages. The DelNS1-M-A14U virus was able to replicate to a level approximately similar to that for the wild-type virus in cells, indicating a functional linkage between the NS1 protein and the transcription or replication of M vRNA. Four mRNAs, M1, M2, mRNA3, and M4, are expressed from M vRNA. DelNS1-M-A14U virus expresses elevated levels of M2 spliced from M1 mRNA while suppressing the expression of mRNA3, linking the role of NS1 with regulation of the alternative splicing of M transcripts. The evidence for the effect of A14U on alternative splicing of M mRNAs came from an analysis of expression of M segments containing A14U and other substitutions, performed in the absence of other viral proteins. The M-A14U segment expresses higher levels of M2 protein, while the level of M1 is unchanged (FIG. 18B), suggesting the A14U substitution favors M2 production by the host splicing machinery.

A14U is situated right within the splice donor site form-RNA3 expression (FIG. 16A), and it seems likely that this substitution abolishes or affects the binding of splicing factors to this motif, leading to the selection of the adjacent splice donor site which produces M2 mRNA instead. This hypothesis is supported by the evidence that other substitutions at this site also enhance M2 expression in the absence of other viral proteins (FIG. 18B). Restoration of NS1 expression by transfecting cells with an NS1-expressing plasmid prior to virus infection significantly increased the M2/M1 mRNA ratio in DelNS1-M-WT virus-infected cells, confirming that NS1 is directly involved in the regulation of M2 mRNA splicing.

The A14U substitution may have dual roles, modulating vRNA synthesis and mRNA splicing, as the levels of M vRNA were significantly enhanced in DelNS1-M-A14U virus infections compared to DelNS1-M-WT infections, while no similar effect was observed for NP vRNA. Therefore, a compound effect of the A14U substitution in the M vRNA 3' promoter region would result in higher efficiency of the viral polymerase complex, generating more vRNA for transcription into mRNA, combined with blockage of the mRNA3 splicing site to allow expression of M2 mRNA. While the NS1 protein is not recognized as an essential element for viral replication, it has multiple functions as an antagonist of host antiviral activity.

Therefore, for a virus lacking NS1 to replicate in cells, alternative viral elements to counter host antiviral activity would be required. The M2 protein has been found to interact with inflammasomes and autophagosomes during influenza virus infection. Thus, M2 may be required to maintain optimal replication for virus under conditions where NS1 is absent and that the A14U adaptive mutant is thus selected to drive expression of higher levels of M2 for such purposes.

Since NS1 interferes with both innate and adaptive immune responses during virus infection and is an influenza virulence determinant, DelNS1 virus is regarded as a promising live attenuated vaccine candidate. Animal experiments show that live attenuated vaccines lacking NS1 may induce better immune responses. However, deletion of NS1 severely affects virus replication, and it is difficult to produce high titers of attenuated virus for vaccine applications. In the previous attempts in the art to propagate NS1-deficient viruses to high titers, DelNS1 virus was found to be restricted to being amplified in limited systems, for example, in an IFN-deficient system or in an NS1-expressing system. The invention demonstrates that a A14U substitution in the NCR of the M segment was sufficient to support replication of DelNS1 viruses to a level close to that of wild-type virus in both MDCK and Vero cells. The effect of the A14U substitution on DelNS1 virus replication in A/WSN/33 and A/PR/8/34 strains can be extrapolated in other influenza virus strains and subtypes.

Example 9—DelNS1 Vaccines Protects Mice from Lethal Dose Challenge of Wild-Type Viruses Inoculation of H7N9 DelNS1 vaccine has no adverse effect on mice and provides full protection to a lethal dose challenge of wild type H7N9 virus. Inoculation of H1N1 DelNS1 vaccine has no adverse effects on mice and is able to provide protection to a lethal dose challenge of wild type H7N9 virus after a slightly delayed response, indicating that DelNS1 vaccine provides cross protection for hetero-subtype virus infection. While split H7N9 vaccine is able to protect mice from lethal challenge, the protective effect is less than with either H7N9 or H1N1 DelNS1 vaccines.

The present invention provides a simple and reliable method to produce any subtype of avirulent strain of influenza A virus via introduction of a substitution in one of the internal genes of the virus. With only a simple modification in one of the internal gene segments, the NS1-deletion viruses can be easily rescued and propagated to high titers, comparable to the wild type virus. In the methods provided by the present invention, the DelNS1 viruses can be easily rescued from regular cell lines without the use of helper viruses and viruses can be propagated to relatively high titers in cells or eggs. A single nucleotide substitution in the M segment of the genome coding for the matrix membrane proteins of the virus is sufficient for the high rescue efficiency of corresponding NS1 deleted virus via reverse genetics. Because of its easy propagation in either Vero cells or eggs and well-characterized safety properties, there are other potential applications of this NS1-del influenza virus vaccine system. In addition to being used as live attenuated vaccine for various subtypes of influenza A virus, including future pandemic strains, the DelNS1 influenza virus vaccine can be used to make vaccine for prevention of other respiratory viral agents which currently still do not have a vaccine. The space generated from the NS1 deletion can be inserted with another gene segment from other viruses, such as MERS coronavirus or EBOLA, to induce cell-mediated immunity to counter infection with these pathogens.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. An attenuated influenza virus, comprising a genetically modified viral genome comprising:

a deletion of an exon region in the non-structural (NS1) coding segment, wherein the deletion results in a knockout of the encoded NS1 protein; and a base substitution in a matrix membrane protein coding segment, wherein the base substitution is selected from a G917A substitution, an A14U substitution, and a combination thereof, wherein base numbering is in accordance with the base numbering of SEQ ID NO: 17.

2. The virus of claim 1, wherein the attenuated influenza virus is attenuated influenza virus strain H7N9.

3. The virus of claim 1, wherein the attenuated influenza virus is attenuated influenza virus strain H1N1.

4. The virus of claim 1, wherein the attenuated influenza virus is attenuated influenza virus strain H5N1.

5. The virus of claim 1, wherein the base substitution is an A14U substitution.

6. The virus of claim 1, wherein the base substitution is a G917A substitution.

7. A vaccine formulation comprising:

an attenuated influenza virus according to claim 1, and a physiologically acceptable carrier.

8. The vaccine formulation of claim 7, wherein the attenuated influenza virus is attenuated H7N9.

9. The vaccine formulation of claim 7, wherein the attenuated influenza virus is attenuated H1N1.

10. The vaccine formulation of claim 7, wherein the attenuated influenza virus is attenuated H5N1.

11. The vaccine formulation of claim 7, wherein the base substitution is an A14U substitution.

12. The vaccine formulation of claim 7, wherein the base substitution is a G917A substitution.

13. A method for generating an attenuated influenza virus according to claim 1, the method comprising:

introducing an influenza virus NS1 gene in which the coding sequence exon has been deleted, into a cell or egg;

introducing a matrix membrane coding sequence of an influenza virus into the cell or egg, wherein the matrix membrane coding sequence comprises one or more base substitutions selected from a G917A substitution, an A14U substitution, and a combination thereof; and wherein the cell or egg comprises the remaining influenza virus gene segments and viral proteins required to produce influenza virus particles; and culturing the cell or egg, wherein the attenuated influenza virus is replicated.

14. The method of claim 13, wherein the influenza virus being attenuated is H7N9.

15. The method of claim 13, wherein the influenza virus being attenuated is H1N1.

16. The method of claim 13, wherein influenza virus being attenuated is H5N1.

17. The method of claim 13, wherein the base substitution is an A14U substitution.

18. The method of claim 13, wherein the base substitution is a G917A substitution.

* * * * *

SEQUENCE LISTING

```
<160> NUMBER OF SEQ ID NOS: 18

<210> SEQ ID NO 1
<211> LENGTH: 27
<212> TYPE: DNA
<213> ORGANISM: Influenza A virus

<400> SEQUENCE: 1

gacatactga tgaggatgtc aaaaatg                                          27


<210> SEQ ID NO 2
<211> LENGTH: 24
<212> TYPE: DNA
<213> ORGANISM: Influenza A virus

<400> SEQUENCE: 2

ctgaaagctt gacacagtgt ttgg                                             24


<210> SEQ ID NO 3
<211> LENGTH: 20
<212> TYPE: DNA
<213> ORGANISM: Influenza A virus

<400> SEQUENCE: 3

cggtctcata ggcaaatggt                                                  20


<210> SEQ ID NO 4
<211> LENGTH: 20
<212> TYPE: DNA
<213> ORGANISM: Influenza A virus

<400> SEQUENCE: 4

caatatccat ggcctctgct                                                  20


<210> SEQ ID NO 5
<211> LENGTH: 20
<212> TYPE: DNA
```

<213> ORGANISM: Influenza A virus

<400> SEQUENCE: 5
ccgaggtcga aacgcctatc 20

<210> SEQ ID NO 6
<211> LENGTH: 20
<212> TYPE: DNA
<213> ORGANISM: Influenza A virus

<400> SEQUENCE: 6
ctctggcact ccttcggtag 20

<210> SEQ ID NO 7
<211> LENGTH: 18
<212> TYPE: DNA
<213> ORGANISM: Influenza A virus

<400> SEQUENCE: 7
agcaaaagca ggcctatc 18

<210> SEQ ID NO 8
<211> LENGTH: 19
<212> TYPE: DNA
<213> ORGANISM: Influenza A virus

<400> SEQUENCE: 8
accgatcttg aggcctatc 19

<210> SEQ ID NO 9
<211> LENGTH: 20
<212> TYPE: DNA
<213> ORGANISM: Influenza A virus

<400> SEQUENCE: 9
caacctccat ggcctctgct 20

<210> SEQ ID NO 10
<211> LENGTH: 20
<212> TYPE: DNA
<213> ORGANISM: Influenza A virus

<400> SEQUENCE: 10
ctttggcact ccttccgtag 20

<210> SEQ ID NO 11
<211> LENGTH: 20
<212> TYPE: DNA
<213> ORGANISM: Influenza A virus

<400> SEQUENCE: 11
ggtgagaatg gacggagaac 20

<210> SEQ ID NO 12
<211> LENGTH: 20
<212> TYPE: DNA
<213> ORGANISM: Influenza A virus

<400> SEQUENCE: 12
ccggctctct ctcacttgat 20

<210> SEQ ID NO 13
<211> LENGTH: 20

<212> TYPE: DNA
<213> ORGANISM: Influenza A virus

<400> SEQUENCE: 13
ccagttccag aaggaggaca 20

<210> SEQ ID NO 14
<211> LENGTH: 20
<212> TYPE: DNA
<213> ORGANISM: Influenza A virus

<400> SEQUENCE: 14
cctgttgtcc caggtgaagt 20

<210> SEQ ID NO 15
<211> LENGTH: 23
<212> TYPE: DNA
<213> ORGANISM: Influenza A virus

<400> SEQUENCE: 15
cccaaggcca accgcgagaa gat 23

<210> SEQ ID NO 16
<211> LENGTH: 21
<212> TYPE: DNA
<213> ORGANISM: Influenza A virus

<400> SEQUENCE: 16
gtcccggcca gccaggtcca g 21

<210> SEQ ID NO 17
<211> LENGTH: 1026
<212> TYPE: DNA
<213> ORGANISM: H1N1 virus

<400> SEQUENCE: 17
agcaaaagca ggttgatatt gaaagatgag tcttctaacc gaggtcgaaa cgtacgttct 60
ctctatcgtc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcacctgcc cagtgagcgg 240
ggactgcagc gtagacgctt tgtccaaaat gctcttaatg ggaacggaga tccaaataac 300
atggacaaag cagttaaact gtataggaag cttaagaggg agataacatt ccatggggcc 360
aaagaaatag cactcagtta ttctgctggt gcacttgcct gttgtatggg cctcatatac 420
aacaggatgg gggctgtgac cactgaagtg gcatttggcc tggtatgcgc aacctgtgaa 480
cagattgctg actcccagca tcggtctcat aggcaaatgg tgacaacaac caatccacta 540
atcagacatg agaacagaat ggttctagcc agcactacag ctaaggctat ggagcaaatg 600
gctggatcga gtgagcaagc agcagaggcc atggatattg ctagtcaggc caggcaaatg 660
gtgcaggcga tgagaaccgt tgggactcat cctagctcca gtgctggtct aaaagatgat 720
cttcttgaaa atttacaggc ctatcagaaa cgaatggggg tgcagatgca acgattcaag 780
tgatcctctc gtcattgcag caaatatcat tggaatcttg cacttgatat tgtggattct 840
tgatcgtctt tttttcaaat gcatttatcg tcgctttaaa tacggtttga aaagagggcc 900
ttctaccgaa ggagtgccag agtctatgag ggaagaatat cgaaaggaac agcagaatgc 960
tgtggatgtt gacgatggtc attttgtcaa catagagctg gagtaaaaaa ctaccttgtt 1020

-continued

```
tctact                                                              1026


<210> SEQ ID NO 18
<211> LENGTH: 1027
<212> TYPE: DNA
<213> ORGANISM: H7N9 virus

<400> SEQUENCE: 18

agcaaaagca ggtagatgtt taaagatgag tcttctaacc gaggtcgaaa cgtacgttct     60

ctctatcatt ccatcaggcc ccctcaaagc cgagatcgca cagagacttg aggatgtttt    120

tgcagggaag aacgcagatc tcgaggctct catggagtgg ataaagacaa gaccaatcct    180

gtcacctctg actaagggga ttttagggtt tgtgttcacg ctcaccgtgc ccagtgagcg    240

aggactgcag cgtagacggt ttgtccaaaa cgccctaaat gggaatggag acccaaacaa    300

catggacaag gcggttaaat tatacaagaa actgaagagg gaaatgacat ttcatggagc    360

aaaggaagtt gcactcagtt actcaactgg tgcgcttgcc agctgcatgg gtctcatata    420

caacagaatg gggactgtga ccgcagaagg ggctcttgga ctagtatgtg ccacttgtga    480

gcagattgct gacgcacaac atcggtccca caggcagatg gcgactacta ctaacccact    540

aattaggcat gagaatagaa tggtactagc cagcactacg gctaaggcta tggagcagat    600

ggctggatca agtgaacagg cagcggaagc catggaagtt gcaagtcagg ctaggcaaat    660

ggtgcaggct atgagaacag ttgggactca ccctaactcc agtacaggtc taaaagatga    720

tcttattgaa aatttgcagg cctaccagaa ccggatggga gtgcaattgc agcggttcaa    780

gtgagcctct agtcgttgca gctaacatta ttgggatatt gcacttgata ttgtggattc    840

ttgatcgtct tttcttcaaa tgcatttatc gtcgttttaa atacggtttg aaaagagagc    900

cttctacgga aggaatacct gagtctatga gggaagaata tcggcaggaa cagcagaatg    960

ctgtggatgt tgacgatggt cattttgtca acatagagct gaagtaaaaa actaccttgt   1020

ttctact                                                             1027
```